United States Patent [19]

Wang

[11] Patent Number: 5,404,754
[45] Date of Patent: Apr. 11, 1995

[54] ULTRASONIC DETECTION OF HIGH TEMPERATURE HYDROGEN ATTACK

[75] Inventor: Weicheng D. Wang, Katy, Tex.

[73] Assignee: Shell Oil Company, Houston, Tex.

[21] Appl. No.: 15,763

[22] Filed: Feb. 10, 1993

[51] Int. Cl.$^6$ ............................................. G01N 29/06
[52] U.S. Cl. ....................................... 73/602; 376/249; 376/252; 73/598; 73/600; 73/630; 73/648
[58] Field of Search ................... 73/599, 600, 602, 597, 73/598, 627, 629, 630, 645, 646, 647, 648, 659; 376/245, 249, 252

[56] References Cited

U.S. PATENT DOCUMENTS

| | | | |
|---|---|---|---|
| 4,596,142 | 6/1986 | Poole et al. | 73/579 |
| 4,750,366 | 6/1988 | Nicolas | 73/602 |
| 4,890,496 | 1/1990 | Birring et al. | 73/597 |
| 5,029,475 | 7/1991 | Kikuchi et al. | 73/602 |
| 5,092,176 | 3/1992 | Buttram et al. | 73/599 |
| 5,197,019 | 3/1993 | Delon-Martin et al. | 73/602 |

OTHER PUBLICATIONS

K. Kawano and A. S. Birring, "Hydrogen Damage Detection by a Nondestructive Technique," Material Performance, Aug. 1989, pp. 71–74.

A. S. Birring, D. G. Alcazar, J. J. Hanley, and S. Gehl, "Ultrasonic Detection of Hydrogen Damage," Materials Evaluation, vol. 47, Mar. 1989, pp. 345–369.

K. Kawano and A. S. Birring, "Hydrogen Damage Detection by a NDT Technique," in the Proceeding of Corrosion Conference at New Orleans, La., Apr. 17–21, 1989, Paper No. 263, pp. 1–14.

A. S. Birring, D. G. Alcazar, J. J. Hanley, G. J. Hendrix, and S. Gehl. Proceedings of the EPRI Conference on boiler Tube Failures in Fossil Plants, EPRI-CS-55-00-SR, "Detection of Hydrogen Damage by Ultrasonics", 1987 pp. 5–59 to 5–75.

M. Yajima, D. Shozen, T. Ohe, "Detection of High-Temperature Hydrogen Attack of Steels by Ultrasonic Testing" Proceedings-American Petroleum Institute, Refining Department V63, 1984, pp. 44–54.

G. P. Singh, "Inspection for Hydrogen Damage in Boiler Waterwall Tubes," Materials Evaluation, vol. 43, Sep., 1985, pp. 1164–1166.

N. O. Cross and A. R. Ciuffreda, "Development and Application of Nondestructive Ultrasonic Test for Detecting High–Temperature Hydrogen Attack of Steels," American Petroleum Institute, Proceeding of the 48th Midyear Refinery Meeting in Los Angels, Calif., May 10, 1983.

T. Watanabe, Y. Hasegawa and K. Kato, "Ultrasonic Velocity Ratio Method for Detecting and Evaluating Hydrogen Attack in Steels," Corrosion Monitoring in Industrial Plants Using Nondestructive Testing and Electrochemical Methods, ASTM STP 908, C. C. Morgan and P. Labine, Eds., American Society for Testing and Materials, Philadelphia, 1986, pp. 153–164.

M. J. Loper, R. D. Shoemaker, and J. G. Stromp, "Mitigating Forced Outages by Selective Replacement of Boiler Tubes", Proceedings of Failures and Inspections of Fossil-Fired Boiler Tubes: 1983 Conference and Workshop, pp. 6.35–6.52, Dec. 1983.

*Primary Examiner*—Hezron E. Williams
*Assistant Examiner*—Rose M. Finley

[57] ABSTRACT

This invention defines a combined inspection procedure using ultrasonic techniques for detection of hydrogen attack damage in material. The procedure comprises an initial scanning procedure for locating areas suspected of being damaged by hot hydrogen. The initial scanning procedure is a pattern-based backscattering test that provides a pattern which is classified as falling within at least one of four backscattering pattern category types. Follow-up test procedures based upon the pattern type are then performed. These tests include spectrum analysis, velocity ratio, spatial averaging backscattering, and frequency dependence for assessing whether the material has hydrogen attack damage and the extent of hydrogen damage in the suspect areas. Should hydrogen attack damage be identified, the velocity ratio and spectrum analysis tests can then be used to determine mechanical properties of the hydrogen attack damaged material.

1 Claim, 20 Drawing Sheets $\Delta t = 15.1145 \mu sec$

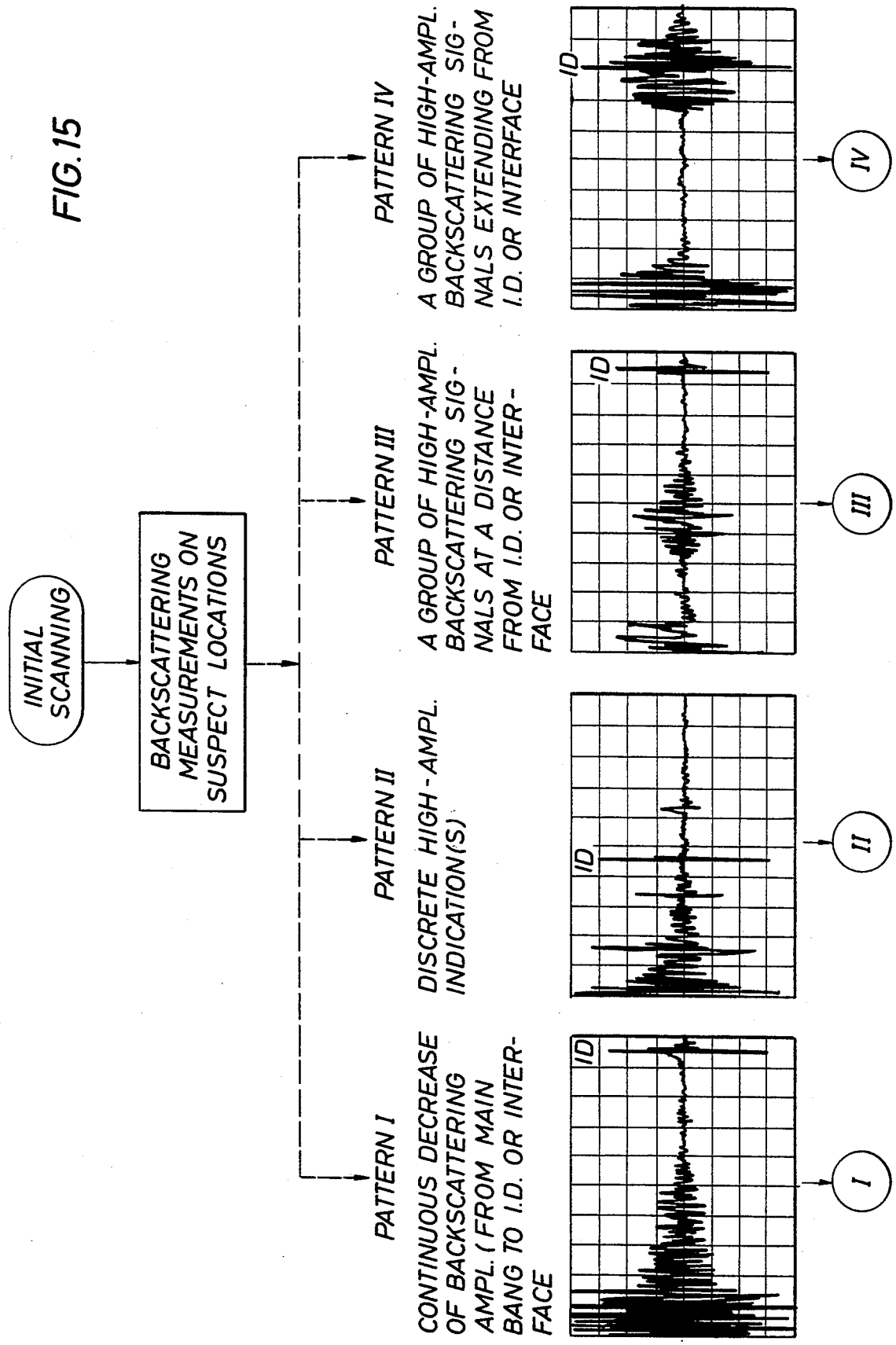

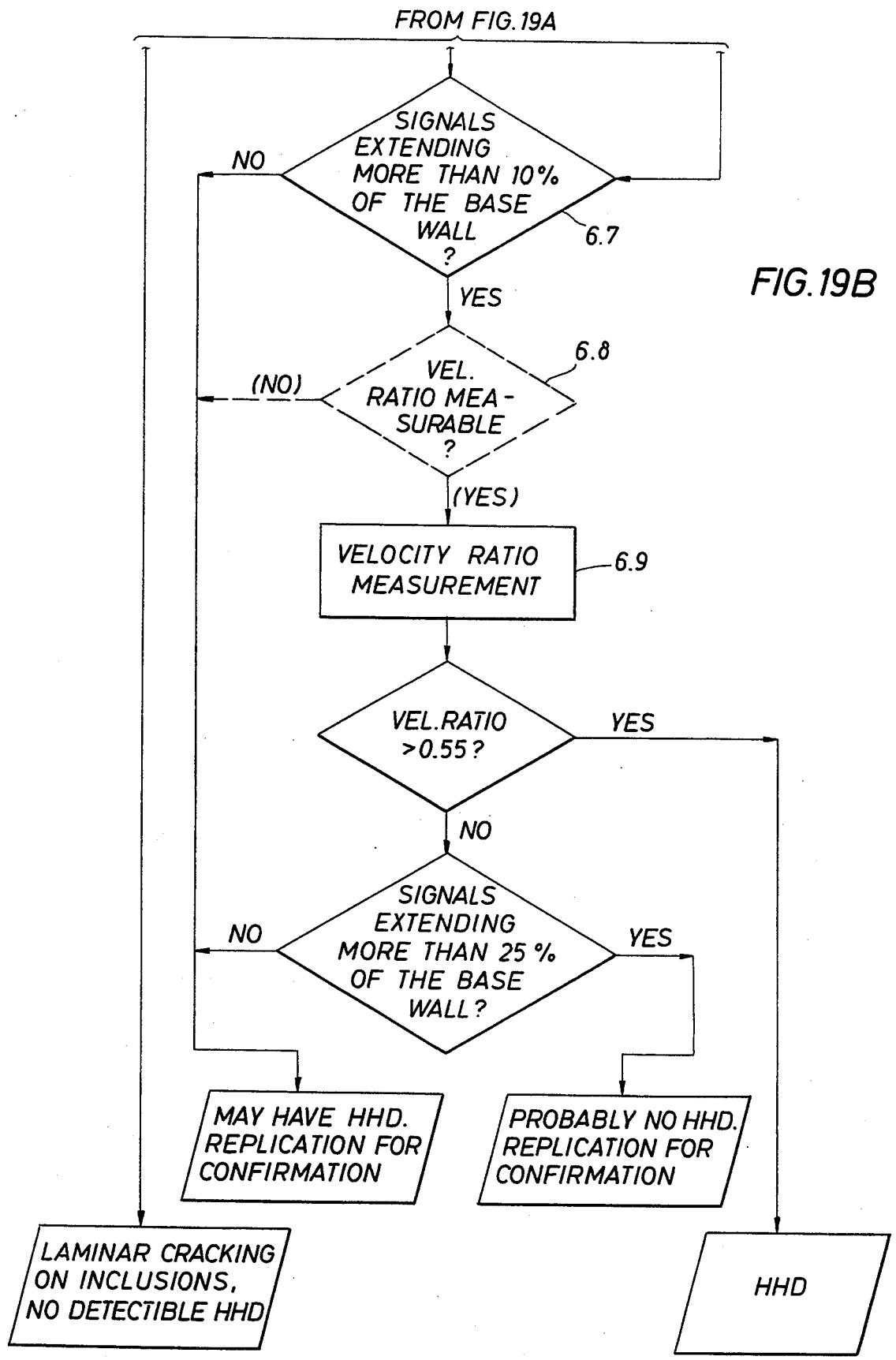

ULTRASONIC DETECTION OF HIGH TEMPERATURE HYDROGEN ATTACK

FIELD OF THE INVENTION

The invention relates to the field of nondestructive evaluation and particularly to ultrasonic inspection for high temperature hydrogen attack and determination of mechanical properties of damaged steels.

BACKGROUND OF THE INVENTION

Hydrogen attack is a damage mechanism occurring in steels exposed to high pressure hydrogen at elevated temperatures. Under such conditions, hydrogen atoms diffuse into steels and react with carbides. The reaction leads to formation of methane and, subsequently, intergranular fissuring and losses of material strength and toughness.

Conventional ultrasonic techniques for finding hydrogen attack are insufficient to identify hydrogen damage against factors such as abnormal grain size, inclusions, rough surfaces, curved internal surface, cladding, disbonds, laminar cracks, and variations of the transducer coupling conditions. Neither can they determine the distance of the damage progression.

Previously, inspection for hydrogen attack relied on five techniques:

1. Echo attenuation/Echo Spectrum

This technique measures the loss of backwall echo amplitudes as an indication of hydrogen damage. It has no ability to discriminate hydrogen attack from abnormal grain size, inclusions, laminar cracks, rough surfaces, non-parallel surfaces, internal surface geometry, cladding, and disbonds between cladding and base metal.

2. Amplitude-based backscatter

This technique measures the amplitude of backscattering signals and uses high backscattering amplitude as the indication of hydrogen damage. It cannot differentiate hydrogen attack from internal flaws such as laminar cracks and inclusions. The validity of the technique also depends on the surface conditions of the calibration material and the material under examination as well as on the pressure applied on the ultrasonic transducer.

3. Velocity ratio

This technique measures the shear-to-longitudinal velocity ratio of the entire wall thickness (i.e., including base metal and cladding material) to assess the extent of hydrogen damage. The result is influenced by cladding materials. Also, it cannot identify hydrogen damage less than 15% of the wall thickness.

4. Creeping Waves/Time-of-Flight Measurement

This technique measures the reduction of creeping wave velocity as the indication of hydrogen damage. It is applicable only to partially damaged steel and only to thin-walled vessels.

5. Pitch-catch mode shear wave velocity

The relative change in shear wave velocity is measured and correlated to the extent of hydrogen damage. The technique cannot differentiate hydrogen attack from change of material thickness. Its sensitivity to hydrogen damage is low, similar to that of the velocity ratio technique.

SUMMARY OF THE INVENTION

This invention is a nondestructive inspection procedure comprising techniques for detecting hydrogen attack and determining the extent of attack in pressure equipment. The inspection relies on seven techniques for finding fissures induced by hydrogen attack.

The first technique, amplitude-based backscatter, identifies areas having backscattering amplitude over a threshold level as suspect locations.

The second technique, pattern-based backscatter, examines the suspect locations and determines a follow-up inspection based on the observed backscattering pattern, which may be one of the following: I) a continuous decrease of backscattering amplitude from the main bang signal to the inside surface or clad/base interface signal (indicating possible through-wall hydrogen attack), II) discrete high-amplitude indications (indicating laminar cracking), III) a group of high-amplitude backscattering signals at a distance from the inside surface or interface signal (indicating midwall inclusions, laminar cracking or growing stage of hydrogen attack), and IV) a group of high-amplitude backscattering signals extending from the inside surface or interface signal (indicating possible initial or growing stage of hydrogen attack).

The third technique, frequency-dependent backscatter, examines the differences between 5 and 10 MHz backscattering patterns. The fourth technique, direction-dependent backscatter, examines the differences between patterns observed from two opposite directions. These two techniques assist in differentiating pattern III from pattern IV, i.e. determining whether internal defects are ID-connected.

The fifth technique, spectrum analysis, measures the frequency dependence of ultrasonic attenuation. Spectra from suspect locations are compared with a reference spectrum to determine the hydrogen-attack-induced attenuation.

The sixth technique, a modified velocity ratio, measures the shear-to-longitudinal velocity ratio of the base metal.

The seventh technique, spatial average backscatter eliminates effects of incoherent ultrasonic signals to reveal backscattering intensity due to hydrogen attack.

Depending on the pattern observed, one or more of the last three techniques are used to completely identify hydrogen attack. For areas identified with hydrogen damage, the distance of the damage progression is determined as the distance between the front end of the high-amplitude backscattering signals and the front end of the internal surface or interface signal.

It is a primary object of the invention to define a nondestructive procedure that can:

i) differentiate hydrogen attack from large grains, inclusions, laminar cracking, cladding, disbonds, rough surfaces, non-parallel surfaces, surface curvature, transducer couplant, and coupling pressure, and ii) determine the distance of hydrogen attack progression.

It is another object of the invention to define a nondestructive procedure which is applicable to steels of any geometry with/without cladding.

Still another object of the invention is to define four ultrasonic techniques: spectrum analysis, pattern-based backscatter, frequency-dependent backscatter, and direction-dependent backscatter.

It is a further object of the invention to modify the conventional "velocity ratio" technique to exclude the effects of cladding on the velocity ratio data.

It is a still further object of the invention to organize the techniques and streamline the inspection procedure such that, in many cases, it requires only three techniques to complete an inspection, which is more than 50% of reduction of the inspection time compared to using all the available techniques.

These inventive procedures are specifically designed for detecting hydrogen attack and determining the distance of hydrogen attack progression in the walls of pressure equipment. The procedures are specifically directed to the inspection of pressure equipment used for high-temperature, high-pressure-hydrogen services; however, the ultrasonic techniques included can be reorganized for other applications such as inspections for creep damage, graphitization, and grain size variations.

BRIEF DESCRIPTION OF THE DRAWINGS

FIG. 15. Backscattering patterns and their corresponding inspection procedures.

DETAILED DESCRIPTION OF THE INVENTION

Throughout this specification, the surface directly exposed to hydrogen is sometimes referred to as "ID" or "inside diameter." The surface not directly exposed to hydrogen is sometimes referred to as "OD" or "outside diameter."

DEVELOPMENT OF BACKSCATTERING THEORY FOR HYDROGEN ATTACK INSPECTION

Scattering of sound waves in hydrogen-damaged materials is affected by the intrinsic material properties (e.g., grain size and inclusion content) as well as by hydrogen-attack fissuring. Assuming that a material is homogeneous before the attack, one can write the attenuation of sound waves in the material as $\alpha(x) = \alpha_0 + \alpha_{HA}(x)$, where $\alpha_0$ is the attenuation coefficient related to the intrinsic material properties and $\alpha_{HA}(x)$ is the coefficient of hydrogen-attack-induced attenuation. The $\alpha_{HA}$ is expressed as a function of distance x because hydrogen attack inclines to the side of material directly exposed to hydrogen. Thus, the intensity of sound waves in hydrogen-damaged material can be written as $$I(x) = I_0 T e^{-2\int_0^x [\alpha_0 + \alpha_{HA}(\tau)]d\tau} \quad (1)$$

where $I_0$ is the intensity of incident sound wave from the transducer, T is the coefficient of sound energy transmitting through the interface between the transducer and the material, and x is the distance from the entry surface. Assuming that the loss of sound wave energy is mainly due to scattering, one can derive and find that the amplitude of backscattering can be approximated as $$A_S(x) = A_0 T \sqrt{2D[\alpha_0 + \alpha_{HA}(x)]\Delta x} \; e^{-2\int_0^x [\alpha_0 + \alpha_{HA}(\tau)]d\tau} \quad (2)$$

where $A_0$ is the amplitude of the incident sound wave, D is the fraction of scattering sound energy going in the direction back to the transducer, and $\Delta x$ is the pulse length.

PATTERN-BASED BACKSCATTER

Equation (2) describes the distribution of backscattering amplitude in the through-wall direction in hydrogen-damaged materials. Considering $\alpha_{HA}$ an index of the severity of hydrogen attack, one can see that hydrogen attack has two opposite effects on the amplitude of backscattering: On one hand, it increases the amplitude through the multiplication term $\alpha_{HA}(x)\Delta x$. On the other hand, it decreases the amplitude through the exponential term. The former effect exists because fissures enhance ultrasonic scattering, and the latter due to high ultrasonic attenuation induced by fissuring.

Figure 1A:
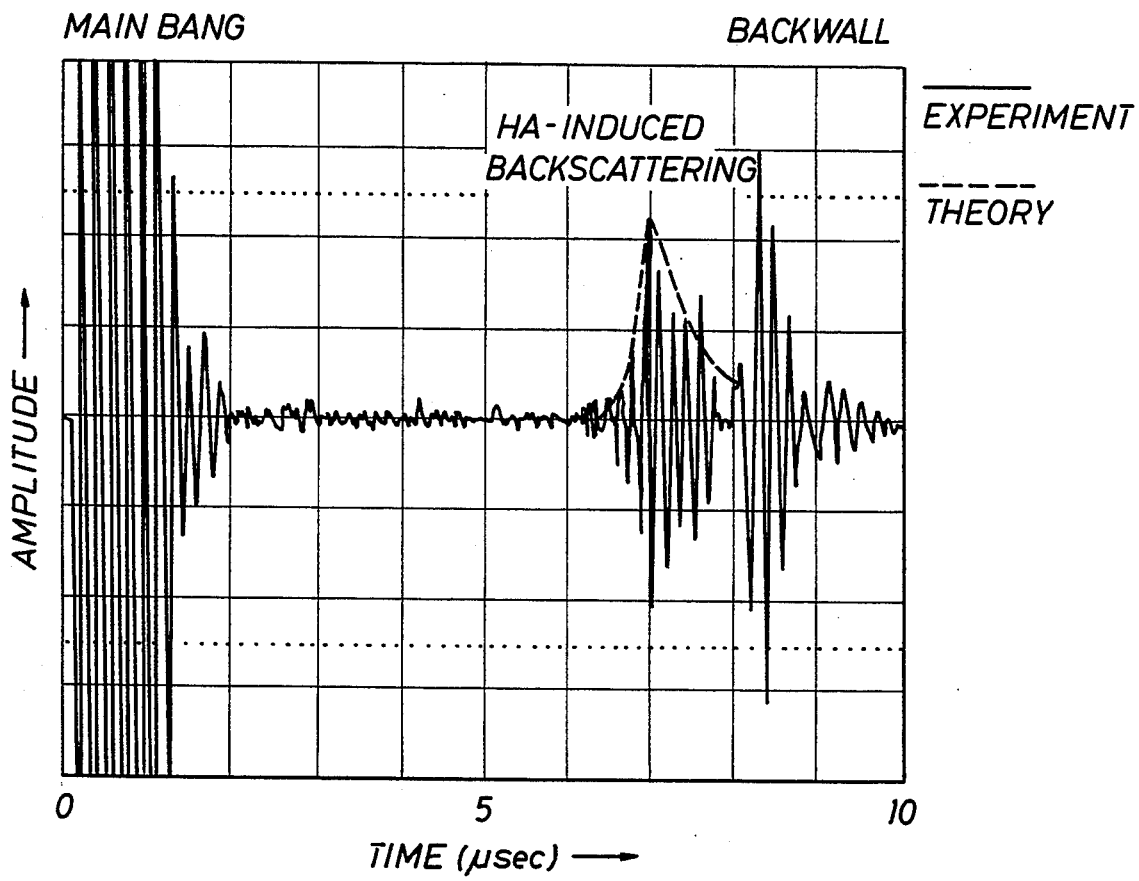
FIGS. 1A–1B Theoretical and measured backscattering amplitude distribution.
Figure 1B:
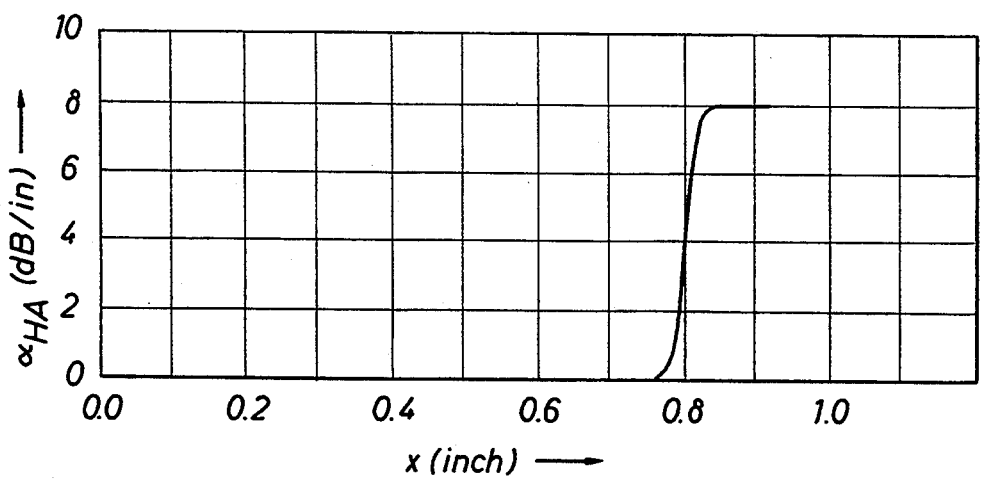

FIG. 1(A) shows an example of results calculated from Equation (2), in comparison with experimental data. The measurement was done on a hydrogen-damaged sample from the non-damaged side with a 10 MHz longitudinal wave transducer. The theoretical curve in (A) was calculated from Equation (2) using $\alpha_0 = 0.005$ and the $\alpha_{HA}(x)$ shown in FIG. 2(B). Both results show a rise-and-fall amplitude distribution as a result of the two effects discussed above. The effect of increasing amplitude dominates at the front end and the effect of attenuation dominates at the rear end of the damage region. Note that the rise of backscattering amplitude coincides with the rise of $\alpha_{HA}$. The depth at which the amplitude rises, therefore, can be regarded as the damage front for determination of the distance of damage progression.

From an inspection view point, it is important to know that backscattering amplitude can actually be lower in regions of more severe damage because of the attenuation effect. Using the absolute amplitude of backscattering to assess the severity of hydrogen damage, therefore, can be quite misleading, especially since the amplitude is also affected by other parameters, as shown in Equation (2). In contrast, the pattern of the amplitude distribution is more dependent on hydrogen attack and less on the other parameters. To identify hydrogen attack by backscattering measurements, one should therefore rely on the pattern, rather than the absolute backscattering amplitude.

FREQUENCY-DEPENDENT BACKSCATTER

Figure 2A:
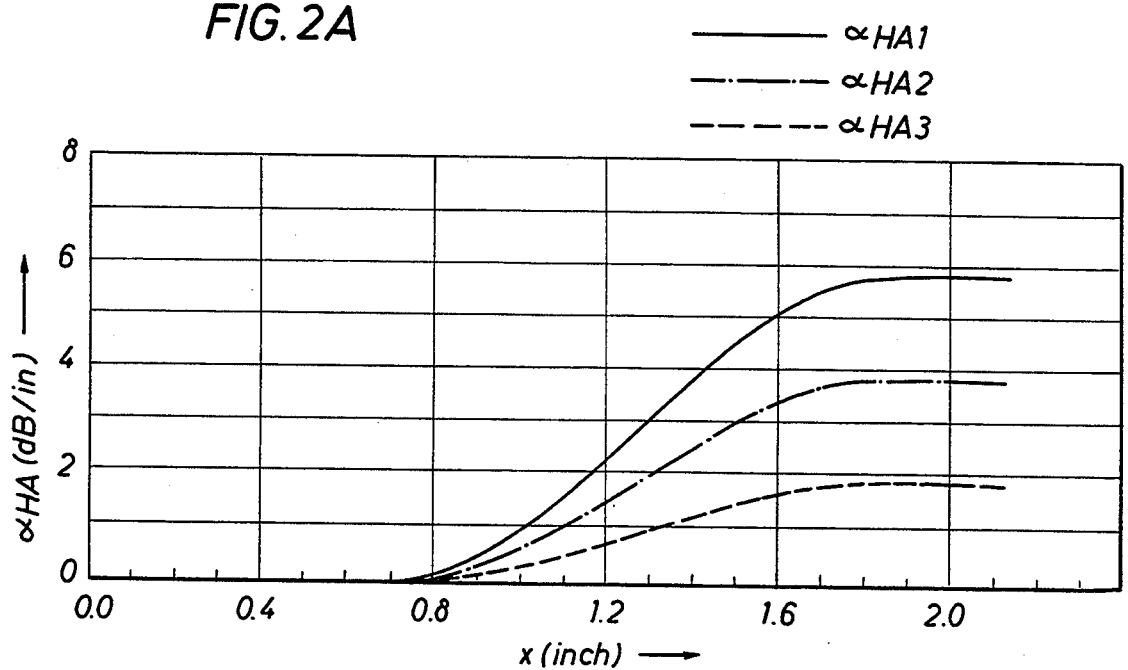
FIGS. 2A–2B Dependence of backscattering patterns on the magnitude of hydrogen-attack-induced attenuation, $\alpha_{HA}$.
Figure 2B:
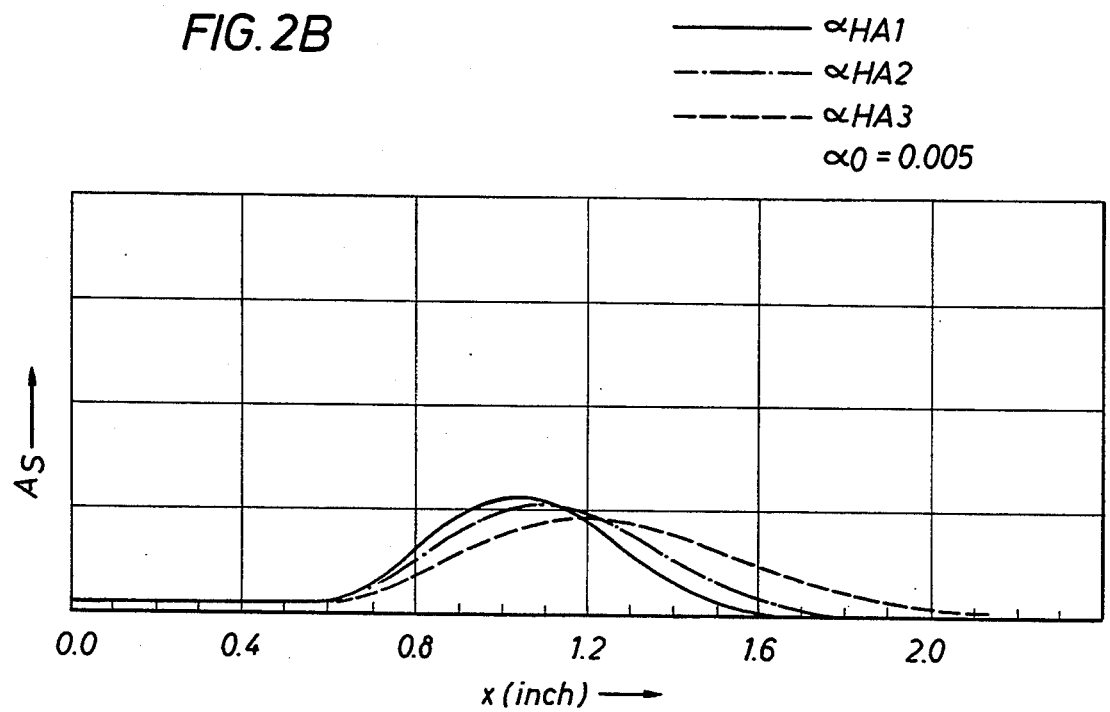
Figure 3A:
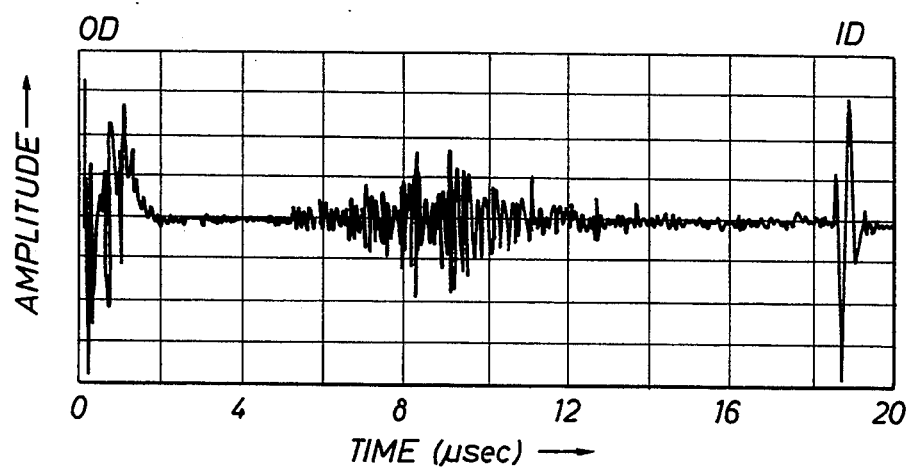
FIGS. 3A–3B Results of backscattering measurements on a hydrogen-damaged sample at two ultrasonic frequencies: (A) 10 MHz and (B) 5 MHz.
Figure 3B:
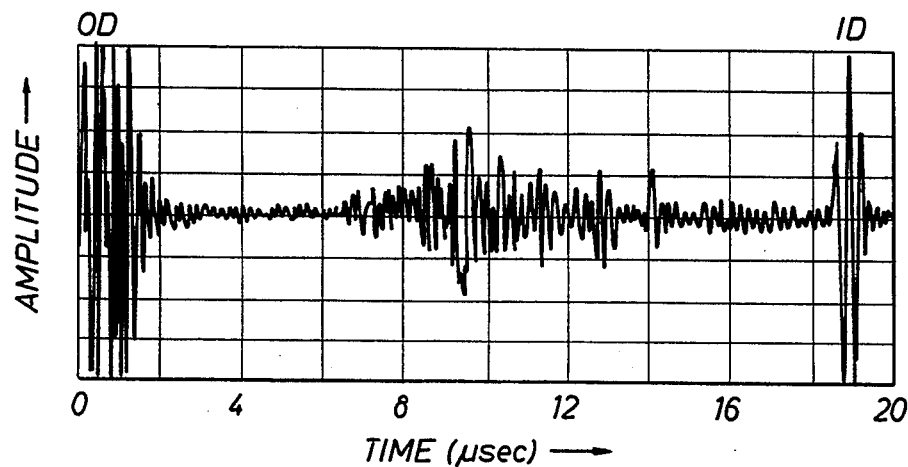

Now let us consider the effects of ultrasonic frequency on backscattering patterns. As will be shown later, decreasing frequency decreases $\alpha_{HA}$. As shown in FIG. 2B this leads to moving backward the peak position and an increase of the tail amplitude relative to the peak amplitude. The patterns in (B) are calculated from Equation (2) using $\alpha_0 = 0.005$ and the $\alpha_{HA}$ values shown in FIG. 2(A). The effect has been proven experimentally, and an example of the results is shown in FIG. 3. As the frequency is reduced from 10 to 5 MHz, the tail amplitude increases correspondingly. This frequency dependence provides a useful means in field inspections for differentiating hydrogen damage from midwall inclusions and laminar cracks. In the latter cases, decreasing frequency would not increase the tail amplitude.

DIRECTION-DEPENDENT BACKSCATTER

Figure 5A:
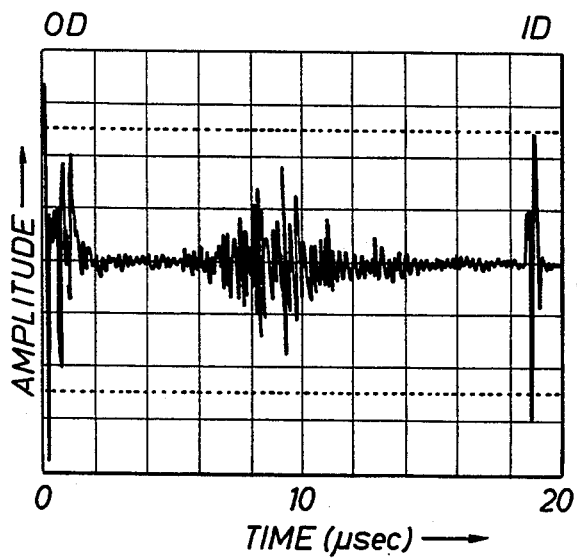
FIGS. 5A–5B Examples of backscattering patterns measured from two opposite directions.
Figure 5B:
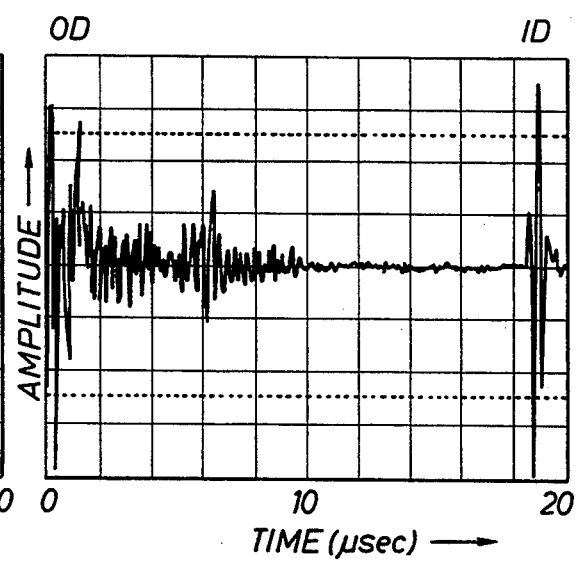
Figure 4A:
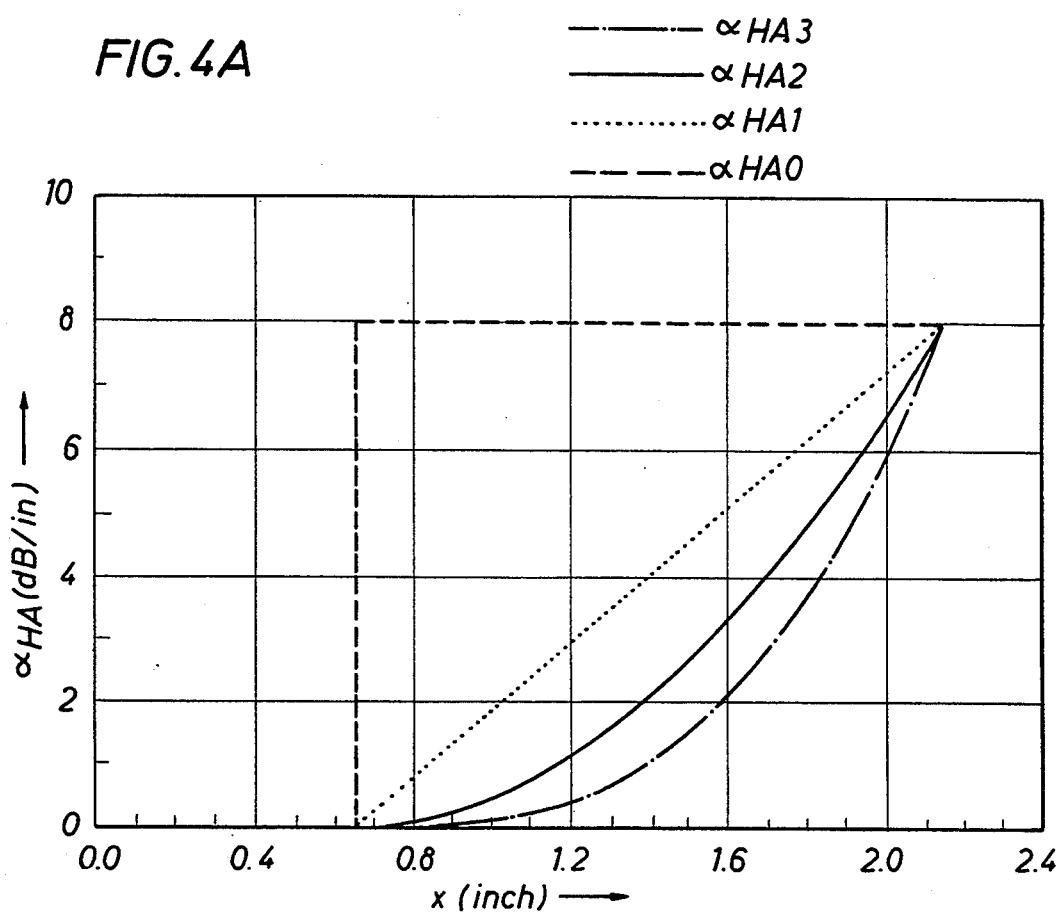
FIGS. 4A–4D Theoretical dependence of backscattering amplitude distributions on measuring direction.
Figure 4B:
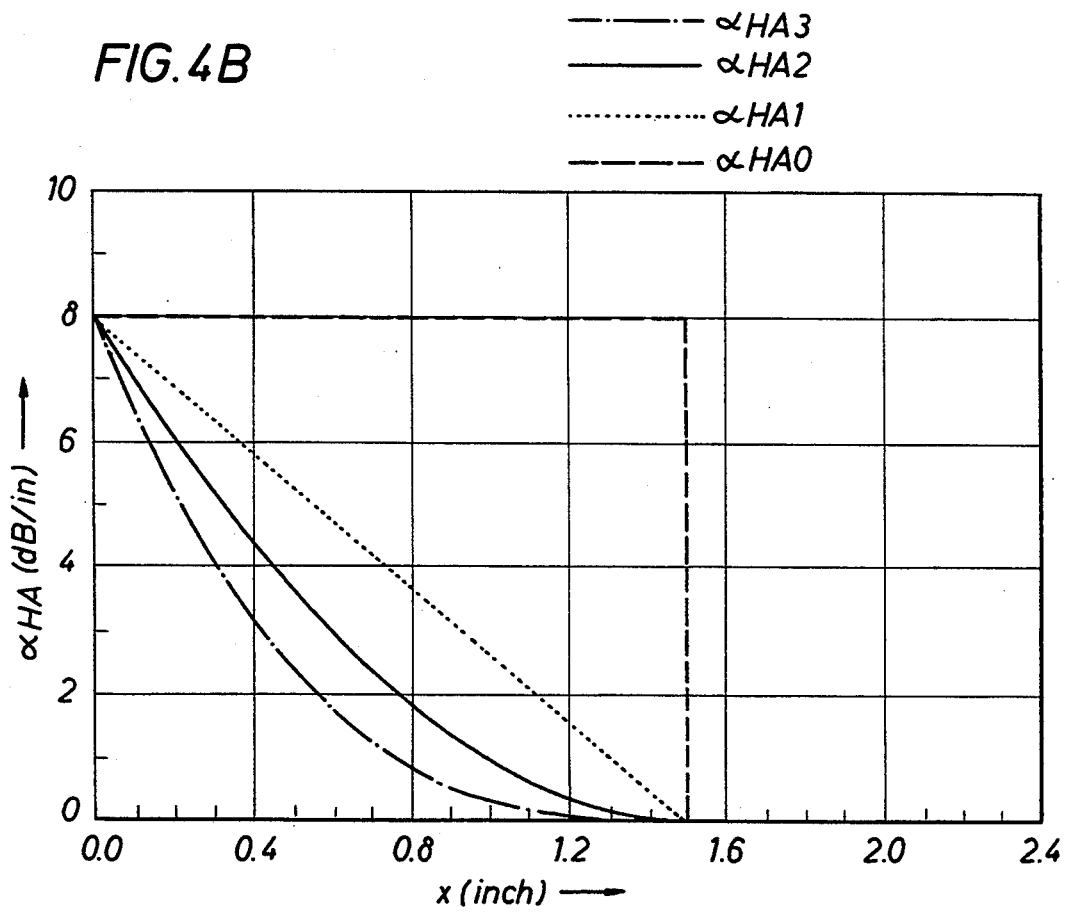
Figure 4C:
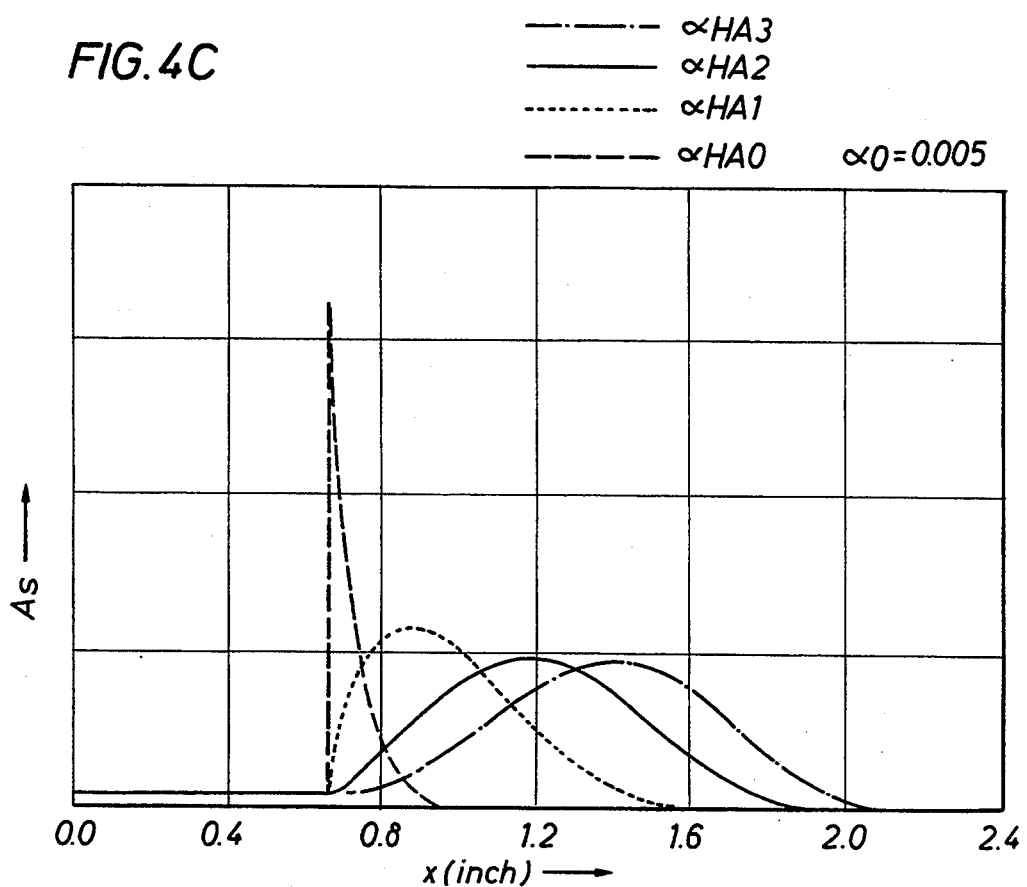
Figure 4D:
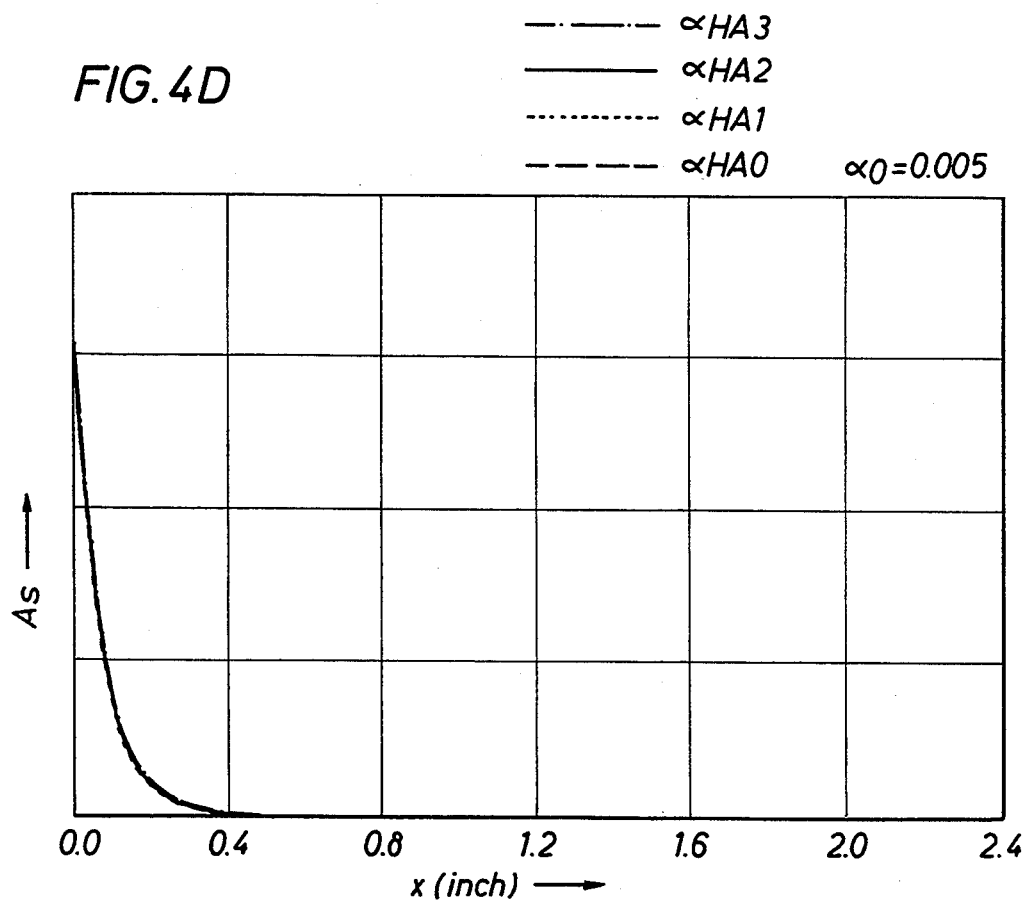

When the damaged side (i.e., the inside of a vessel) is accessible, backscattering measurements can also be done from the damaged side. FIG. 4 shows the theoretical variations of backscattering patterns due to a change in measuring direction. FIGS. 4 (C) and (D) are backscattering amplitudes calculated from Equation (2) using the $\alpha_{HA}$ distributions shown in FIGS. 4 (A) and (B), respectively. Instead of the rise-and-fall patterns shown in FIG. 4(C), in FIG. 4(D) the peaks are pushed to the front and thus there is only a continuous decrease of backscattering amplitude. Such a change of pattern is confirmed experimentally, as shown in FIG. 5, which shows backscattering patterns measured from (A) the outside surface OD (i.e., the non-damaged side and (B) the inside surface ID (i.e., the damaged side) of a hydrogen-damaged heat exchanger. The measurements were done with a 10 MHz longitudinal wave transducer. The drastic change of backscattering pattern due to the change of measuring direction gives us an additional means to discriminate hydrogen attack from inclusions and laminar cracking. In the latter cases, backscattering indications would stay at the same distance to one side of the material regardless of the measuring direction.

MEASUREMENTS OF PATTERN-BASED, FREQUENCY-DEPENDENT AND DIRECTION-DEPENDENT BACKSCATTER

Required equipment for conducting backscattering measurements includes an oscilloscope capable of performing signal averaging, such as a LeCroy Model 9420 350 MHz digital oscilloscope, a pulser/receiver unit, such as Panametrics Model 5052UAX50 Ultrasonic Analyzer, an output device, such as a Hewlett Packard 7470A plotter, a broad-band 10 MHz/0.5" longitudinal wave transducer, such as Panametrics V-111, and a broad-band 5 MHz/0.5" longitudinal wave transducer, such as Panametrics V-109. Any commercially available ultrasonic couplant is acceptable. Shear-wave couplant, such as Krautkramer Branson SLC 70, is preferred. The system configuration may be, for example, as in FIG. 9. The pulser/receiver should be adjusted such that the system will have the maximum amplitude response to high frequencies and have a continuous decrease of the ring-down amplitudes prior to coupling the transducer to the part surface. Typical control settings for a Panametrics pulser/receiver and a LeCroy oscilloscope may be as follows:

1) Panametrics pulser/receiver:
   Pulse-echo mode,
   Rep Rate 1 KHz,
   Damping at Variable, fully clockwise
   Energy 1,
   Gain at 40 dB,
   RCVR ATTN 2 dB,
   HP Filter 1 MHz,
   Main-bang gate mode; Gate delay at Low, fully counter-clockwise; and Gate width at Low, fully counter-clockwise.
2) LeCroy oscilloscope:
   Channel 1 with 1 Meg-ohm AC coupling,
   External trigger at normal mode, AC coupling, positive
   slope, and Trigger level at 0.2 V.

The procedure is as follows:

Couple a 10 MHz transducer to the part surface and adjust the oscilloscope to display the backscattering signals between the main bang and the first backwall signals on the oscilloscope. Perform temporal averaging of the signals. Release the transducer when the average finishes. Record the averaged signal display as the result of the measurement. See FIG. 10 for examples showing: (A) Pattern I—a continuous decrease of backscattering amplitude from the main bang to the backwall echo; (B) Pattern II—discrete high-amplitude backscattering indications; (C) Pattern III—a group of high-amplitude backscattering signals at a distance from the backwall echo; and (D) Pattern IV—a group of high amplitude backscattering signals extending from the backwall echo.

For frequency-dependent backscatter, repeat the procedure using a 5 MHz longitudinal wave transducer.

For direction-dependent backscatter, use the same 10 MHz transducer and system settings, but also measure backscatter patterns from the ID surface.

SPATIAL AVERAGING BACKSCATTERING MEASUREMENTS

Spatial averaging backscattering measurements eliminate the effects of incoherent ultrasonic signals to reveal backscattering intensity due to hydrogen attack. To perform spatial-average backscatter measurements, the pulser/receiver should be capable of giving rectified signals, or the oscilloscope should be capable of performing mathematical treatments to obtain the absolute value or the square of signal amplitude.

Figure 11:
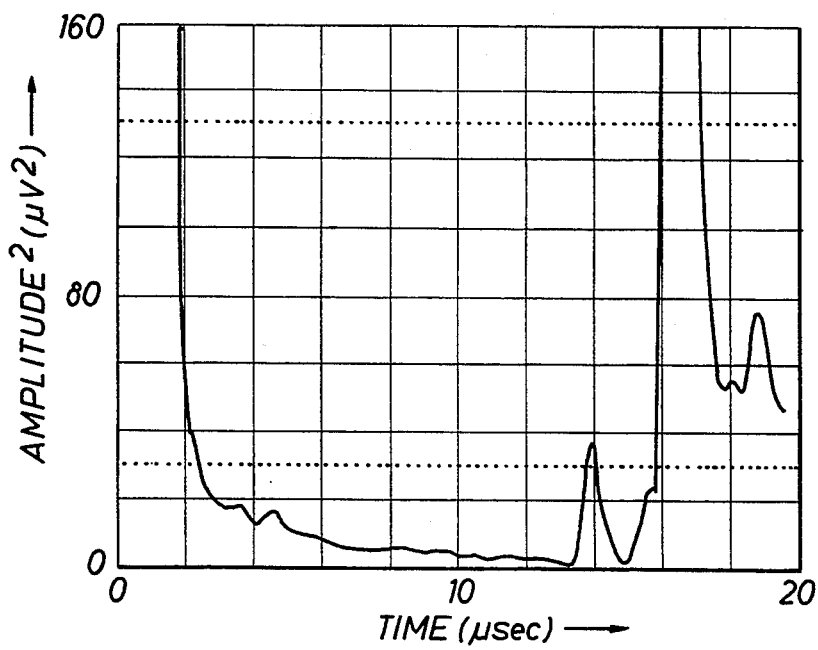
FIG. 11 Typical result of spatial-averaging backscattering measurements.

With the system configured as in the preceding section, couple the transducer to the part surface and adjust the oscilloscope to display the backscattering signals between the main bang and the first backwall signals. Perform temporal averaging of the rectified signals, or of the RF signals after amplitude squaring, (i.e. of $A^2$ where A is the amplitude). Simultaneously, move the transducer at the inspection location, for example, within a 1" diameter area. The transducer movement should be kept low enough, e.g. at a speed under 0.5 inch/sec., to maintain a proper contact to the part surface. Release the transducer when the average finishes. Plot the averaged display as the result of the measurement. See FIG. 11 for an example of output.

SPECTRUM ANALYSIS

Wave scattering at fissures can also be quantified through attenuation measurements. Previous attempts failed in the field because the effect of hydrogen attack was not discriminated from effects of other parameters such as grain size, inclusions, cladding, and surface geometry. This problem can be solved if we measure attenuation in the frequency domain and use deconvolution to cancel out the effects of other parameters. This is done by subtracting the spectrum of the first backwall echo in the inspected location from the spectrum of a reference location which has the same metallurgical and structural conditions but without hydrogen damage. The subtraction (i.e., deconvolution) yields a net quantity:

$$20\log\left(\frac{A_{REF}}{A}\right) = (20\log e) <\alpha_{HA}> (2d_{HA}) \qquad (3)$$

where $A_{REF}$ and $A$ are, respectively, the spectra of the reference and inspection locations, $<\alpha_{HA}>$ is the mean value of the coefficient of hydrogen-attack-induced attenuation within the damaged thickness $d_{HA}$.

Figure 6A:
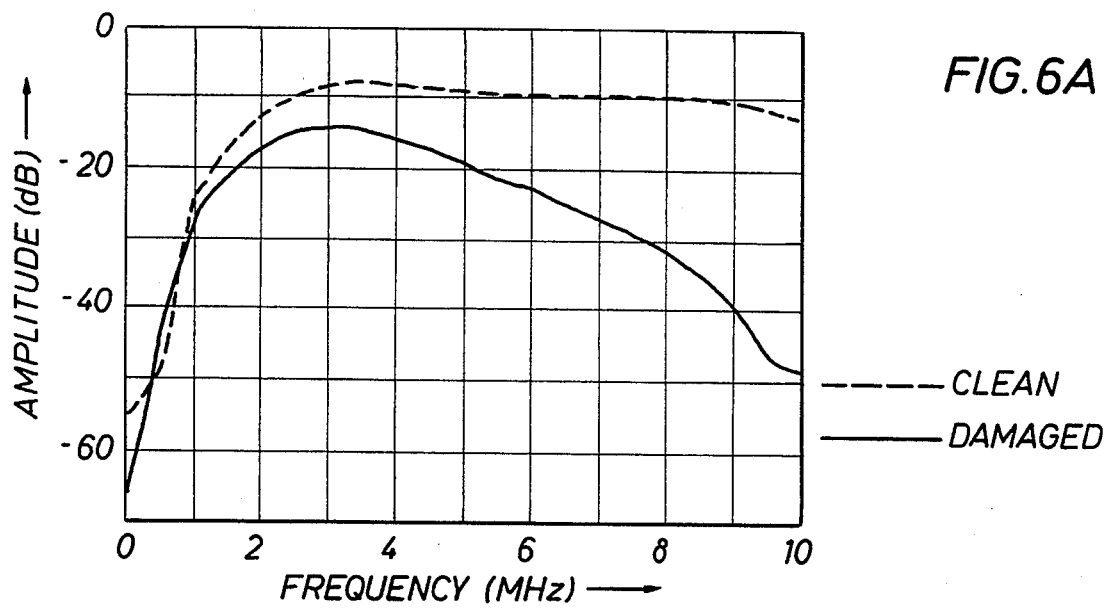
FIGS. 6A–6B (A) Spectra measured from clean and through-wall-damaged 0.5" thick, carbon-½ Mo steel samples. (B) The resultant spectrum from deconvolution.
Figure 6B:
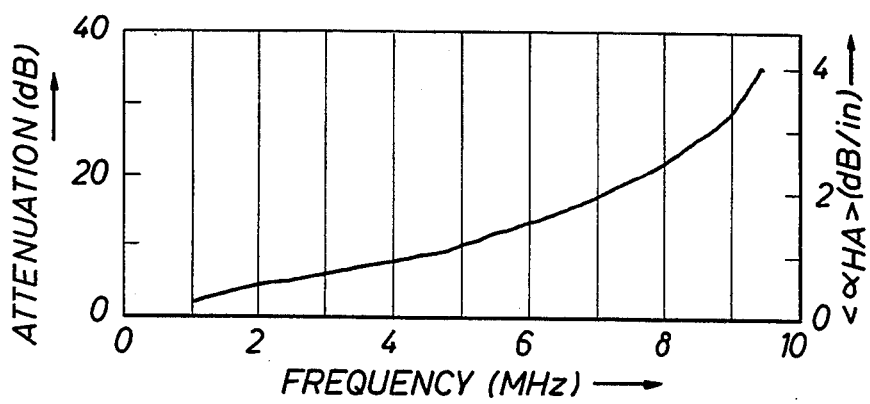

FIG. 6(A) shows an example of spectra measured from clean (i.e., non-damaged) and damaged carbon-½ Mo steel samples. The deconvolved result (FIG. 6B) reveals a clear increase of attenuation with the increase of frequency. The attenuation in (B) is equal to the 20 log($A_{REF}/A$) shown on the left-hand side of Equation (3). This frequency dependence is used to identify hydrogen damage, i.e. attenuation that does not increase with the increase of ultrasonic frequency should not be misinterpreted as hydrogen attack. Also, using the distance of damage progression, $d_{HA}$, determined from backscattering measurements, one can calculate $<\alpha_{HA}>$ from Equation (3) as a measure of the mechanical properties of the damaged material.

CONDUCTING SPECTRUM ANALYSIS MEASUREMENT

The test set-up is configured as in FIG. 9 except that instrument settings are changed as follows:
  Pulser/receiver
    Damping at 25 ohms
    Energy at 3
    High Pass (HP) filter at 0.3 MHz
  Oscilloscope Time/Expansion is set at 0.2 μsec/div.

Couple the transducer to the part surface. Adjust the Trigger Delay knob on the oscilloscope to place the 1st backwall echo on the oscilloscope screen. (The pulser/receiver gate can also be used if no visible distortion of the signal display is introduced by the gate.) Use the following tests to examine the backwall echo for signal saturation.

Waveform Tests: Set the receiver attenuation (RCVR ATTN) at 2 dB. Adjust the Amplitude knob on the oscilloscope to keep the peak amplitude of the backwall echo within 100% of the full screen height. Increase the RCVR ATTN on the pulser/receiver and adjust the amplitude knob to keep the peak amplitude within 20%–100% of the full screen height. The signal is not saturated when a further increase of the RCVR ATTN changes only the amplitude but not the waveform of the signal.

6 dB Test Adjust the Amplitude knob on the oscilloscope to set the peak amplitude of the backwall echo at 80±10% of the full screen height. Increase the RCVR ATTN of the pulser/receiver by 6 dB. The echo signal is saturated if the peak amplitude does not decrease to half of its previous level.

Figure 12A:
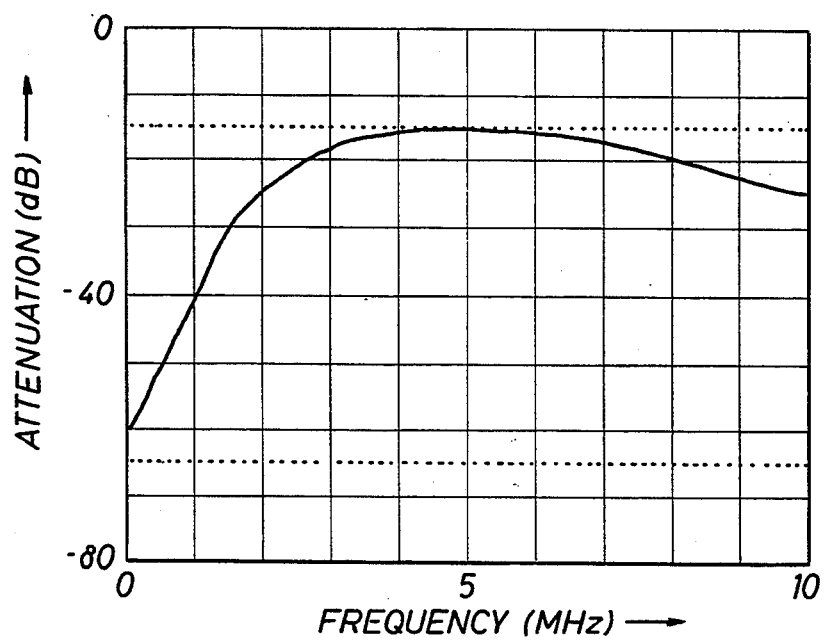
FIGS. 12A–12B Examples of (A) a measured spectrum and (B) frequency-dependent attenuation.
Figure 12B:
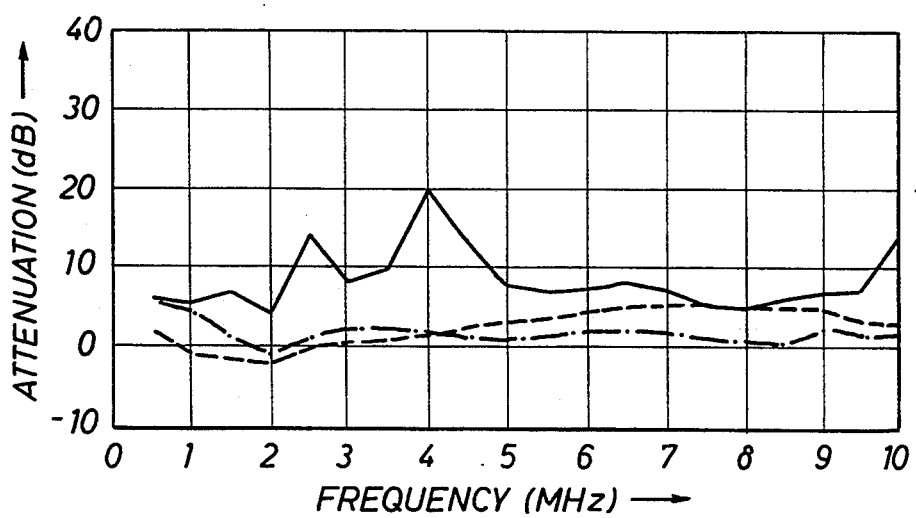

Adjust the receiver attenuation until the lowest value without signal saturation is obtained. Record the value and label it as RA (in dBs). Maintain the setting and adjust the Amplitude knob to set the peak amplitude of the 1st backwall echo at 80±10% of the full screen height. Hold the transducer in firm contact with the part surface and perform temporal averaging of the signal. Release the transducer when the average finishes. Perform a Fourier transformation converting the averaged signal from the time domain to the frequency domain. An example is shown in FIG. 12(A). Display the spectrum in the frequency range from 0.5 to 10 MHz. Record the amplitude in dB as a function of frequency from 0.5 to 10 MHz with an increment of, e.g. 0.5 MHz. Label the result as $A_R(f)$. Calculate and record $A(f) = A_R(f) + RA$. Determine the frequency-dependent attenuation by using the equation: $ATT(f) = [A_{ref}(f) - A(f)]$, where $A_{ref}(f)$ is the reference spectrum of the same material thickness. An example of $ATT(f)$ printout is shown in FIG. 12B.

OBTAINING A REFERENCE SPECTRUM

Use the same equipment, instrument settings (except for RCVR ATTN, which should be determined by the waveform and 6 dB tests), and transducer as those used in measuring spectra of the part under inspection. Employ one of the two methods described below to obtain the reference spectrum.

Method 1:
  Use a clean calibration block or a clean location of the same thickness as the part under inspection. Perform steps as described above to obtain a spectrum, with correction of the RA value, from the block or from the clean location. The resultant spectrum, with correction of the RA value, is the reference spectrum $A_{ref}(f)$.

Method 2:
  If a clean calibration block or a clean location of a particular thickness d cannot be obtained, find two clean calibration blocks of thicknesses $d_1$ and $d_2$, where $d_1 < d < d_2$ and $d_1$ and $d_2$ are within 20% deviation of d. Measure the first-backwall-echo spectra from the two calibration blocks. Add the respective RA values. Label the results as $A_1(f)$ and $A_2(f)$. Calculate the reference spectrum for thickness d as $A_{ref}(f) = [(d/d_1)A_1(f) + (d/d_2)A_2(f)]/2$.

MODIFIED VELOCITY RATIO

Velocity ratio measures the ratio of longitudinal-to-shear transit times as the shear-to-longitudinal velocity ratio, i.e., $\Delta t_L/\Delta t_S = V_S/V_L$. The ratio is a function of the fissure density and the material chemistry. When performing the technique on clad equipment, one should measure the time of flight in the base metal, instead of the whole wall thickness, to avoid the effect of cladding chemistry.

VELOCITY RATIO MEASUREMENT

Equipment and Settings

Figure 9:
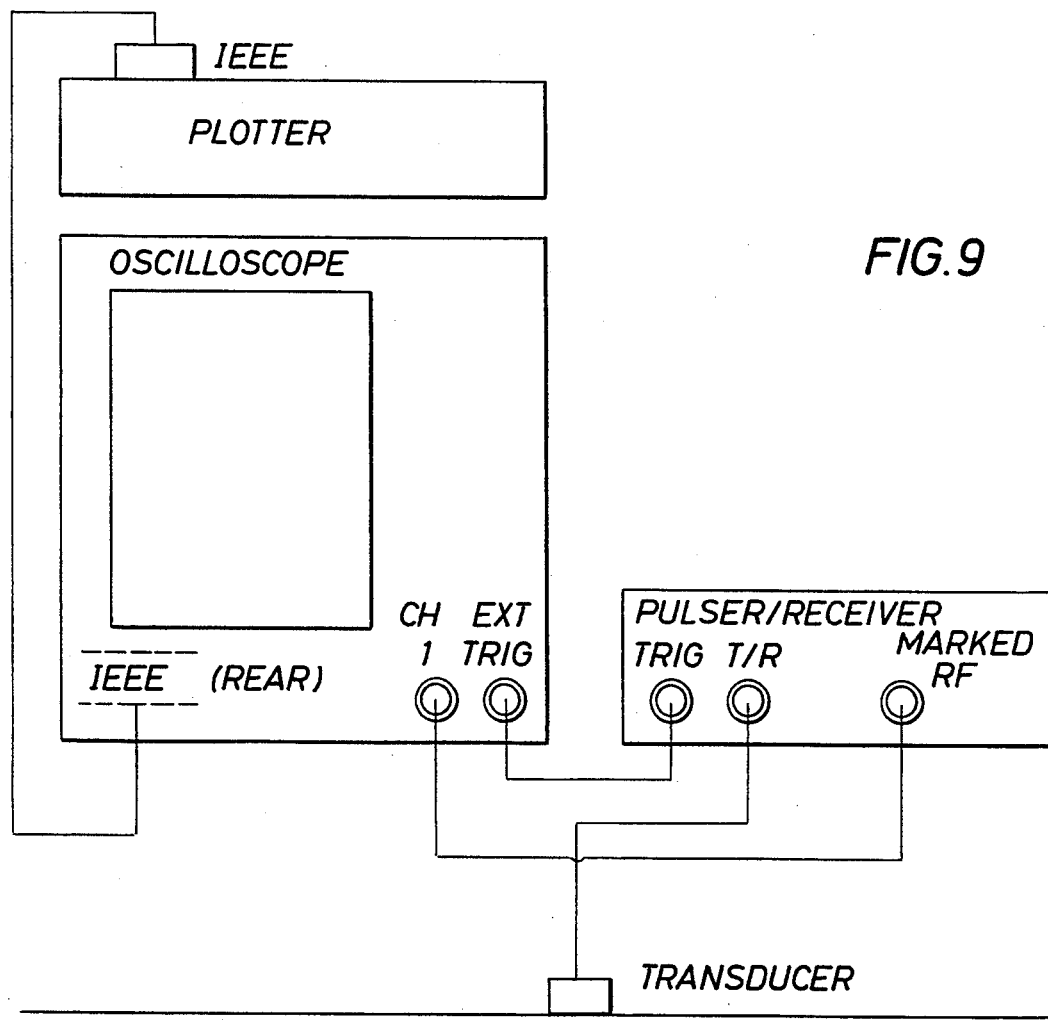
FIG. 9 Schematic of system test configuration.
Figure 10A:
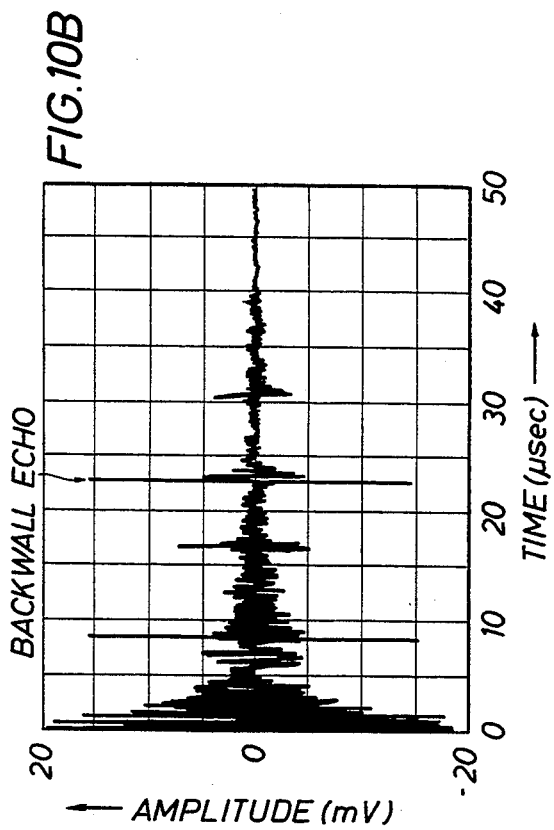
FIGS. 10A–10D Backscattering patterns.
Figure 10B:
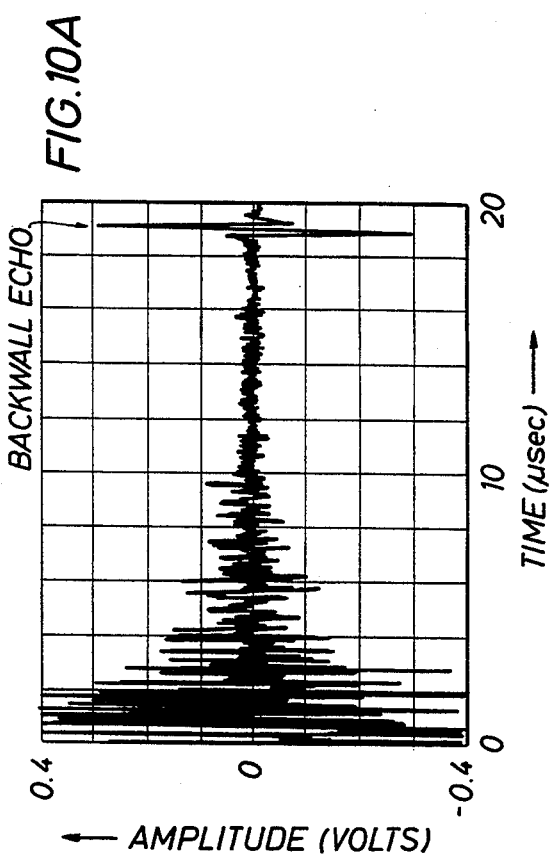
Figure 10C:
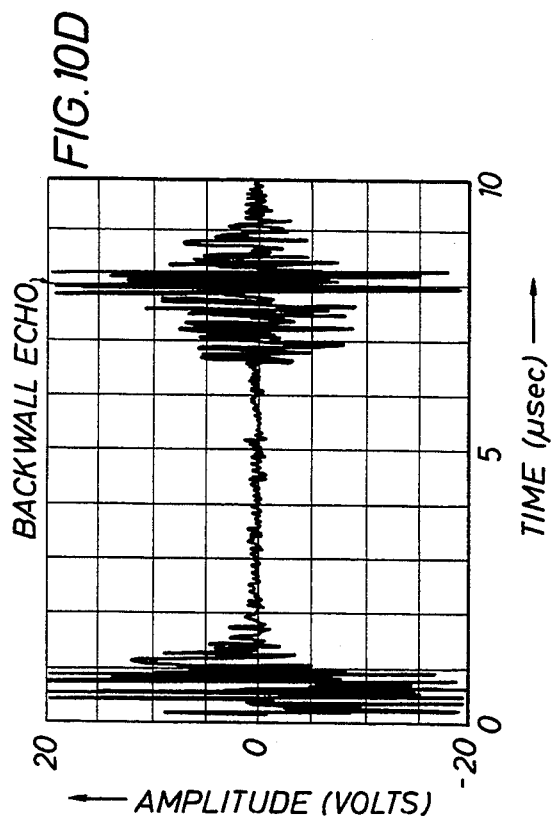
Figure 10D:
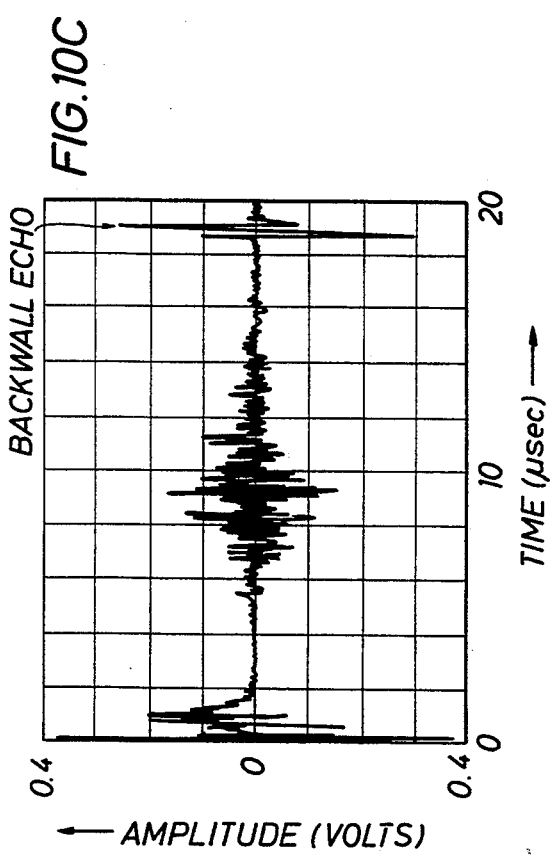

The equipment is set up as in FIG. 9. Broad-band, 5 MHz/0.5" longitudinal wave and shear wave transducers, such as Panametrics V-109 and V-155 are required.

Instrument Settings may be as follows:
1) Panametrics pulser/receiver unit:
   Pulse-echo mode,
   Rep Rate 1 KHz,
   Gain at 40 dB,
   HP filter 0.3 MHz,
   Main-bang gate mode, Gate delay at low, fully counterclockwise, and Gate width at low, fully counterclockwise.
2) LeCroy oscilloscope:
   Settings are the same as for backscattering measurement.

Figure 13A:
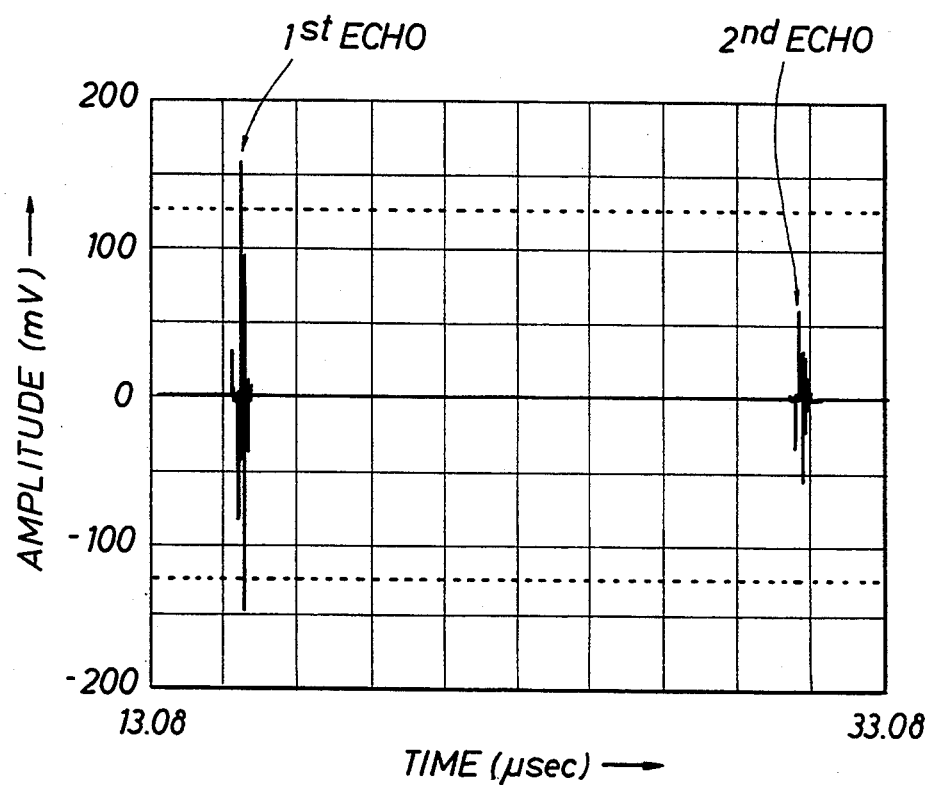
FIGS. 13A–13B Measurements of velocity ratios from bare metals.
Figure 13B:
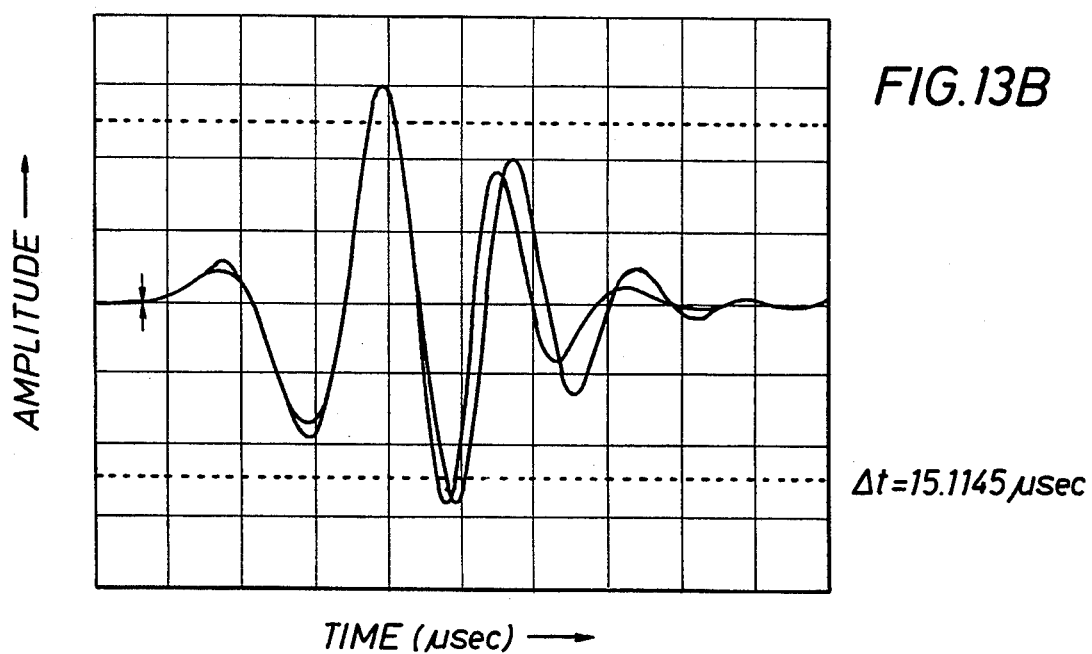
Figure 14A:
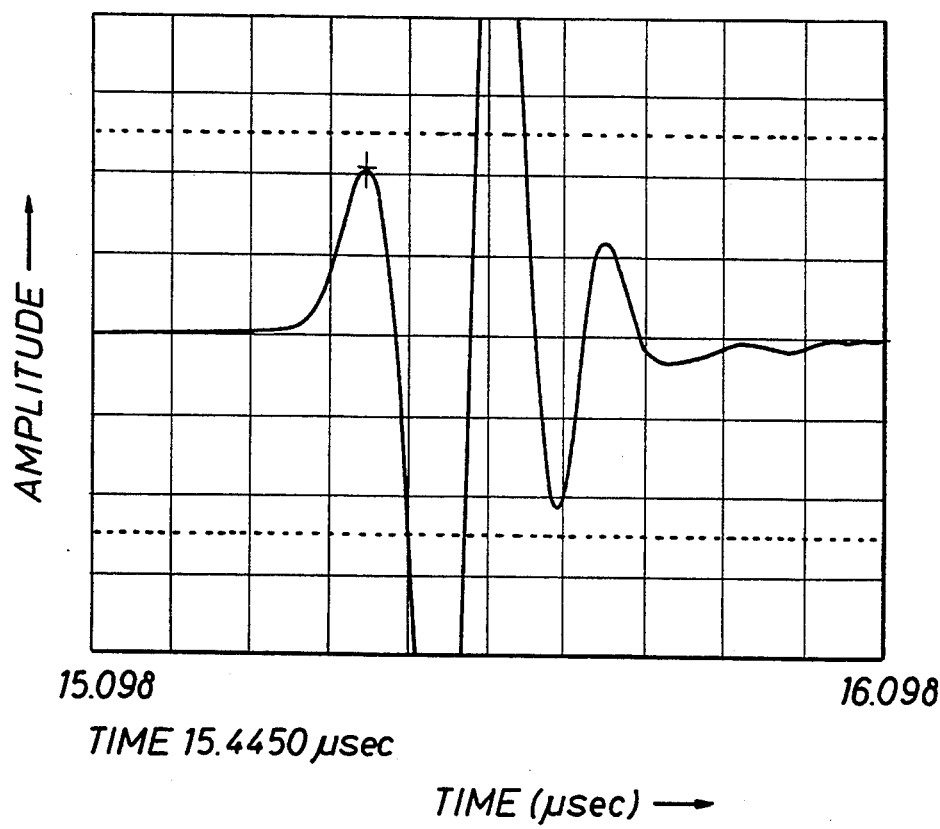
FIGS. 14A–14B Measurements of velocity ratios from clad equipment.
Figure 14B:
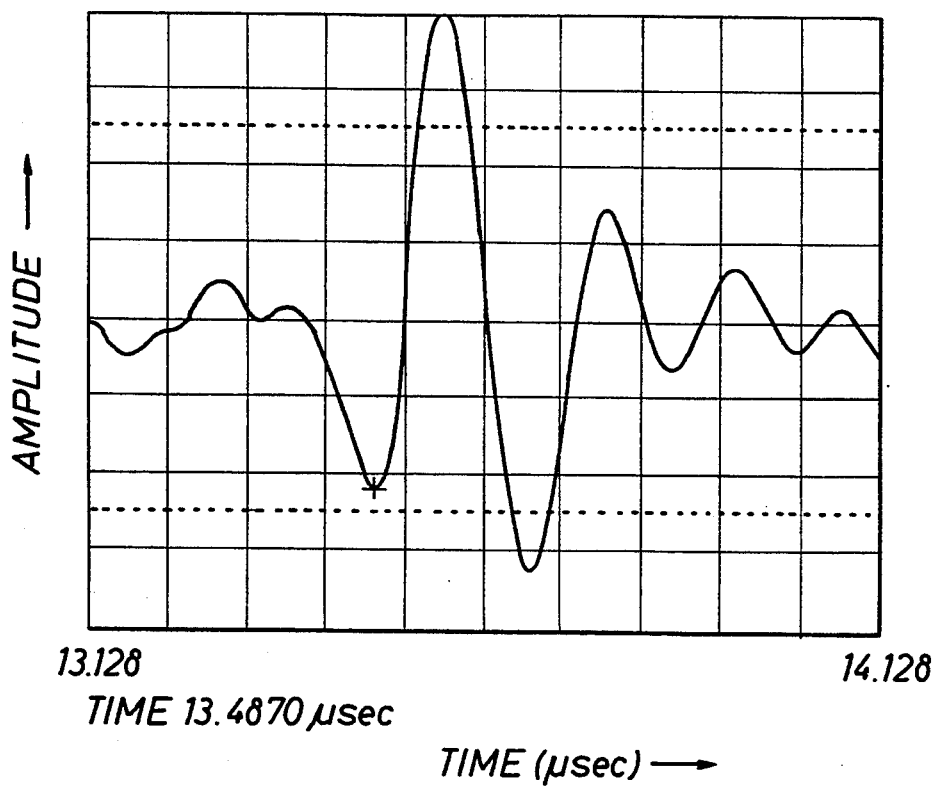

Method 1: Measurement of Velocity Ratios from Bare Metals
1. Couple the transducer to the part surface and display the 1st and 2nd backwall echoes on the oscilloscope screen, as shown in FIG. 13A. Use method 2 if the second backwall echo cannot be clearly observed.
2. Adjust the RCVR ATTN on the pulser/receiver and use the 6 dB test previously described to keep the 1st backwall echo from saturation.
3. Perform a temporal average of the signals. Release the transducer when the average finishes.
4. Measure the time of flight between the two echoes, for example, by overlapping the two echoes, as shown in FIG. 13B. Record the time of flight as $\Delta t_L$ for longitudinal wave and $\Delta t_S$ for shear wave measurements.
5. Calculate and record the velocity ratio as $V_S/V_L = \Delta t_L/\Delta t_S$ Method 2: Measurement of Velocity Ratios from Clad Equipment
1. Use a 5 MHz/0.5" longitudinal wave transducer and perform steps 1–4 of method 1 on a clean calibration block. Record the measured time of flight between the first and second backwall echoes as $\Delta t_{L2}$.
2. Without changing the trigger delay, the pulser/receiver settings or the transducer, measure from the same block the delay time of the first peak of the first backwall echo, as shown in FIG. 14A, as $\Delta t_{L1}$.
3. Calculate $\Delta t_{LC} = \Delta t_{L1} - \Delta t_{L2}$.
4. Repeat step 2 or the material under test to measure the delay time of the first peak of the cladding interface signal (for clad equipment) or the backwall echo (for equipment without cladding). Note that a clad interface signal may have phase reversal as shown in FIG. 14B. Record the time as $\Delta t_{L1}$.
5. Calculate $\Delta t_L = \Delta t_{L1} - \Delta t_{LC}$.
6. Repeat steps 1–5 with a 5 MHz/0.5" shear wave transducer to obtain $\Delta t_S = \Delta t_{S1} - \Delta t_{SC}$, where $\Delta t_{SC} = \Delta t_{S1} - \Delta t_{S2}$.
7. Calculate the velocity ratio as $V_S/V_L = \Delta t_L/\Delta t_S$.

DETERMINATION OF MECHANICAL PROPERTIES

Figure 7:
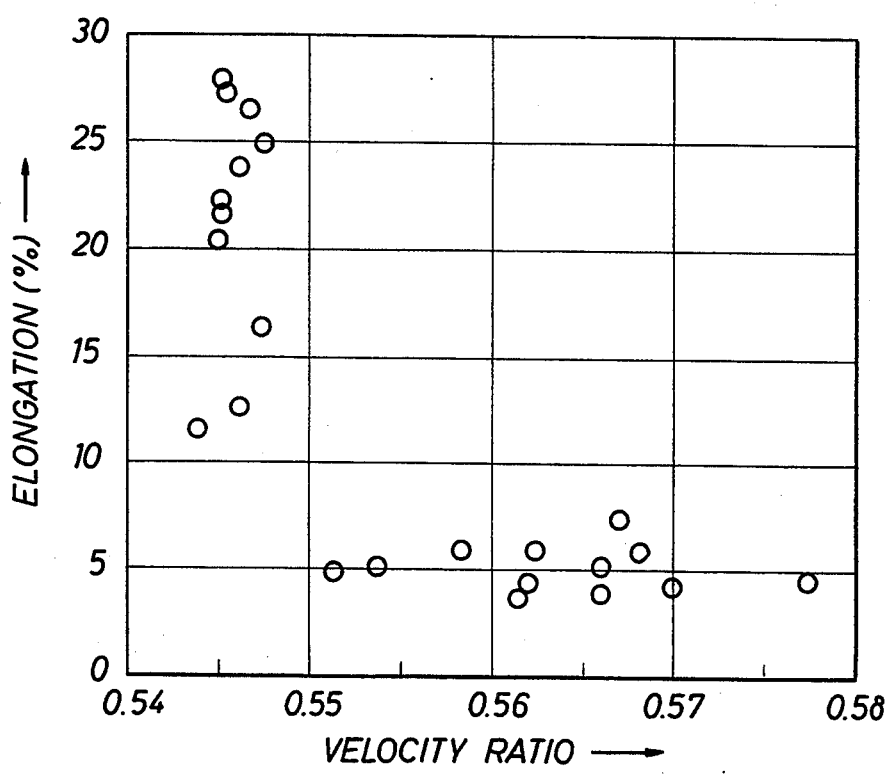
FIG. 7 Percentage of elongation (from tensile tests) versus velocity ratio for determination of damaged mechanical properties.

Both $<\alpha_{HA}>$ and $V_S/V_L$ can be used to quantify the mechanical properties of damaged materials. An example of the correlation between the ultrasonic parameters and mechanical properties is shown in FIG. 7, where the percentage of tensile elongation is plotted against velocity ratio. The data were measured from hydrogen-damaged carbon-½ Mo steel samples.

Figure 8:
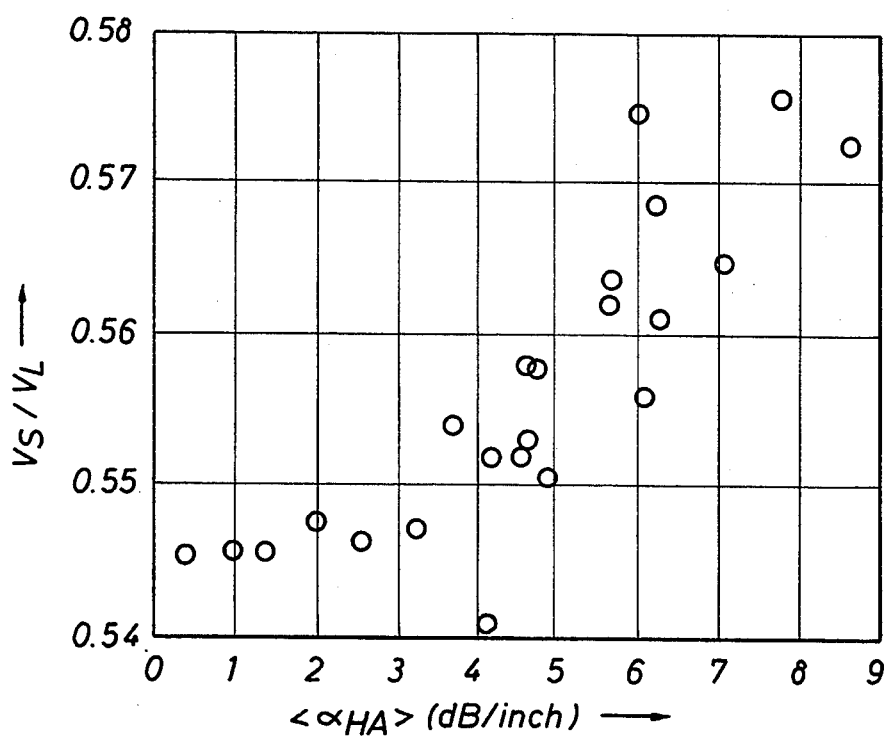
FIG. 8 Relation between velocity ratio, $V_S/V_L$ and the mean value of hydrogen-attack-induced attenuation within a damaged region, $<\alpha_{HA}>$ at 8 MHz.

Although both $<\alpha_{HA}>$ and $V_S/V_L$ can be used to assess mechanical properties, they do not have the same sensitivity. FIG. 8 shows the relation between $V_S/V_L$ and $<\alpha_{HA}>$ at 8 MHz. The data were measured from damaged carbon-½ Mo steel samples. While the attenuation coefficient $<\alpha_{HA}>$ has increased 3 dB/inch, the velocity ratio stays nearly the same, below 0.55. The relation suggests that to assess mechanical properties of damaged materials with high sensitivity one should use attenuation instead of the velocity ratio.

COMBINED PROCEDURE

Part 1. Initial scanning using amplitude-based backscatter to identify suspect locations for follow-up inspection:

The initial scanning procedure requires a longitudinal wave 10 MHz/0.5" transducer, such as Panametrics transducer V-111, and one of the following equipment or equivalent: (1) a Rutherford B-SCAN system, such as a Rohback Cosasco System model TMI-150, (2) an A-scan screen imaging ultrasonic flaw detector, such as Panametrics flaw detector EPOCH 2100 and Krautkramer-Branson Model USL-48, and (3) a C-scan system with the DAC (distance amplitude correction) capability. Most standard ultrasonic couplants are acceptable. Ultragel II, Krautkramer Branson SLC 70, and water (for B-scan system) have been found to work well.

Flat bottom holes of depths equal to 25±5%, 50±5%, and 75±5% of the examination part thickness are used to calibrate the equipment. The holes are drilled in a reference block of the same nominal composition and thermal treatment as the part to be examined. The flat bottoms of the holes should be within 1° of parallel to the examination surface, and the holes should be 3/64" in diameter. The surface of the reference block should have a surface finish of 64 micro-inches (equivalent to 200 grit sand blast).

The material to be examined should have a surface finish of 64 micro-inches maximum.

Couple and position the search unit for maximum amplitudes from the 25%±5%, 50±5%, and 75±5% deep reflectors. Set the instrument to produce a 75±5% of full scale indication from the reflector giving the highest amplitude. Without changing the instrument setting, couple and position the search unit over each of the holes and mark on the screen the maximum amplitude from each hole. Draw a line connecting the maximum amplitude marks for the 25%, 50%, and 75% deep flat bottom holes. Extrapolate the line to 100% depth on the CRT. This line is the 100% DAC (distance amplitude correction curve).

Scan at a rate not to exceed the ability of the operator to observe and comprehend any valid ultrasonic signals. Nor should the scanning rate exceed the ability of the equipment to record and display data. Generally, this should be less than 6 inch/sec.

Scanning shall cover 100% of the specified surface, with the search unit being indexed between each pass such that there is at least 15% overlap of adjoining passes in order to assure adequate coverage for locating hydrogen damage.

Record all areas where indications exceed 100% DAC.

Where recordable conditions listed in the above step are detected, continuously scan the entire area adjacent to the indications that exceed 100% DAC. Mark the boundaries of each recordable area on the part inspected.

Sketch and/or photograph each recordable area, showing the locations in sufficient detail to locate them at a later time.

Part 2. Follow-up inspection using pattern-based backscatter, frequency-dependent backscatter, direction-dependent backscatter, spatial-average backscatter, spectrum analysis and modified velocity ratio:

Additional calibration blocks may be needed in some of the following steps. These additional blocks include clean and damaged calibration blocks. Both clean and hydrogen-damaged calibration blocks of thicknesses within 20% of the part thickness of the inspected material are preferred. The blocks should be of the same nominal composition as the material to be examined. The damaged block(s) should contain through-wall hydrogen damage, and the metallographs of the blocks should be included in the final report. The surface finish of the calibration blocks should have a surface finish of 16 micro-inches.

The locations for the following inspection should be prepared to a surface finish of 32 micro-inches maximum.

1. Conduct backscattering measurements using a 10 MHz longitudinal wave transducer.
2. Proceed to steps 3, 4, 5, or 6 based on the backscattering pattern observed, as shown in FIG. 15:

I) A continuous decrease of backscattering amplitude from the main bang signal to the backwall echo or the interface signal (of clad equipment). Proceed to step 3 and inspection procedure diagrams (A) and (B) of FIG. 16.

II) Discrete high-amplitude backscattering indications. Proceed to step 4 and inspection procedure diagrams (A) and (B) of FIG. 17.

III) A group of high-amplitude backscattering signals at a distance from the backwall echo or the interface signal (of clad equipment). Proceed to step 5 and inspection procedure diagrams (A) and (B) of FIG. 18.

IV) A group of high-amplitude backscattering signals extending from the backwall echo or the interface signal (of clad equipment). Proceed to step 6 and inspection procedure diagrams (A) and (B) of FIG. 19.

Figure 16A:
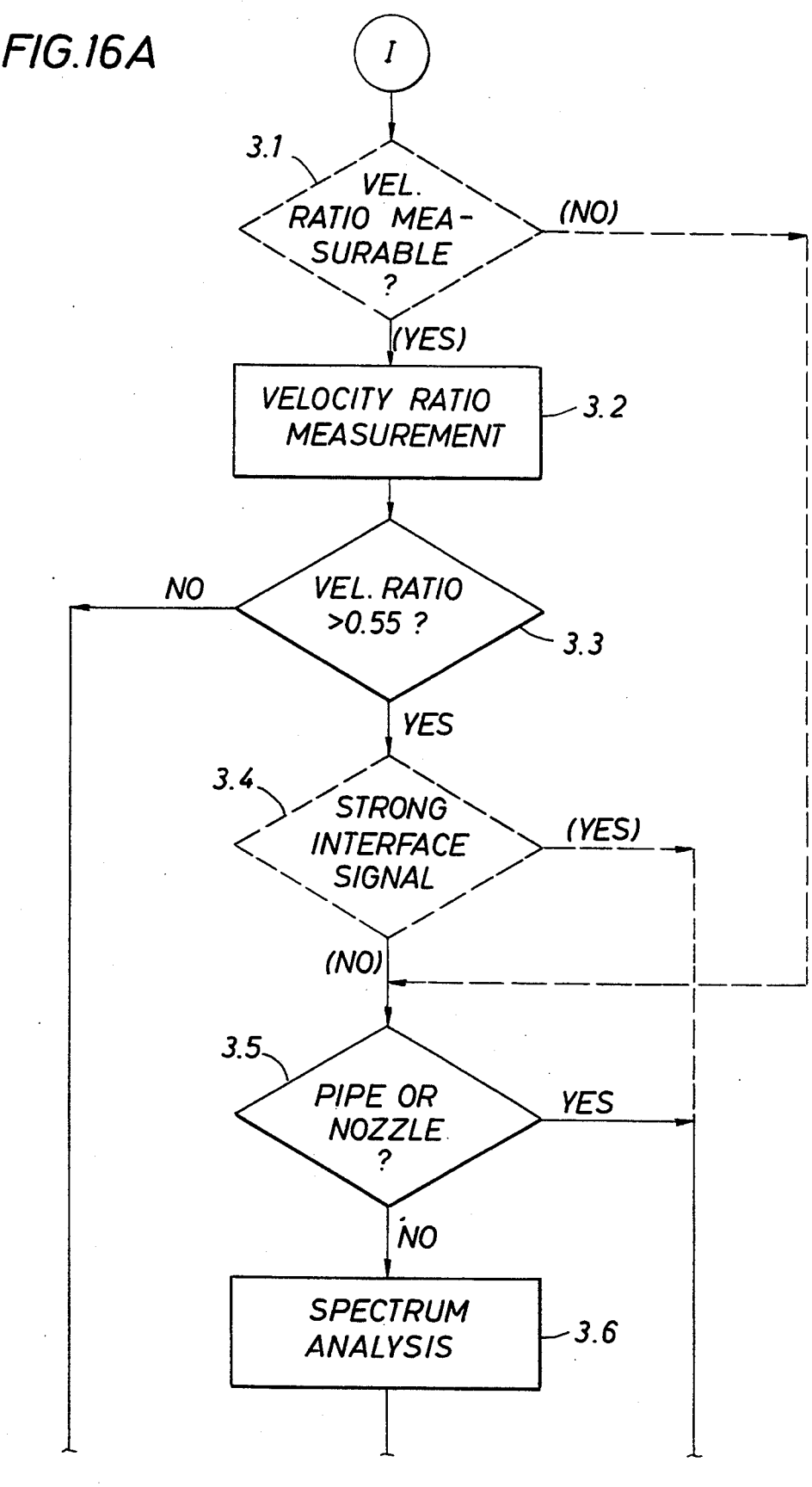
FIG. 16. Inspection procedure for locations showing Pattern I waveform.
Figure 16B:
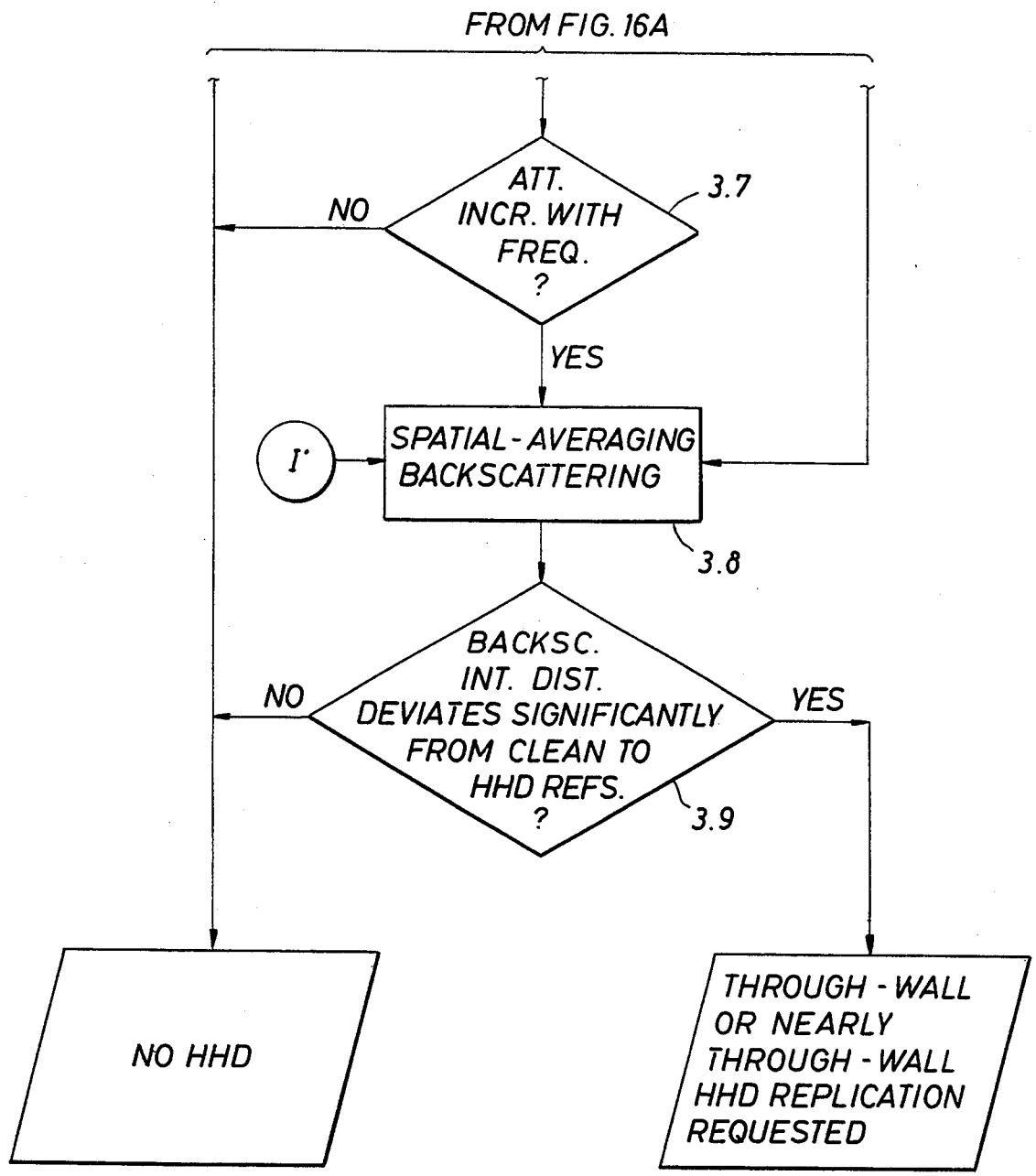

3. Pattern I: A continuous decrease of backscattering amplitude from the main bang signal to the backwall echo or the interface signal (of clad equipment). The inspection procedure in this case is shown in FIG. 16 and described as follows. (Dashed lines indicate steps pertaining to inspection of clad equipment only.)

3.1 Skip steps 3.2–3.4 if the interface signal is not clear enough for velocity ratio measurements (for clad equipment only).

3.2 Conduct velocity ratio measurements.

3.3 If the velocity ratio is not greater than 0.55, measurements are completed for this spot.

3.4 Skip steps 3.5–3.7 if the interface signal amplitude is greater than 5% of the backwall echo amplitude (for clad equipment only).

3.5 Skip steps 3.6 and 3.7 if the part under inspection is a piece of pipe or nozzle.

3.6 Conduct spectrum analyses using clean calibration block(s) as the reference.

3.7 If the resultant attenuation does not increase with frequency, measurements are completed for this spot.

3.8 Conduct spatial-averaging backscattering measurements.

3.9 Does backscatter intensity distribution of the spatial-averaging backscattering measurements deviate significantly from clean to hydrogen damaged (HHD) references!. Measurements are completed.

Figure 17A:
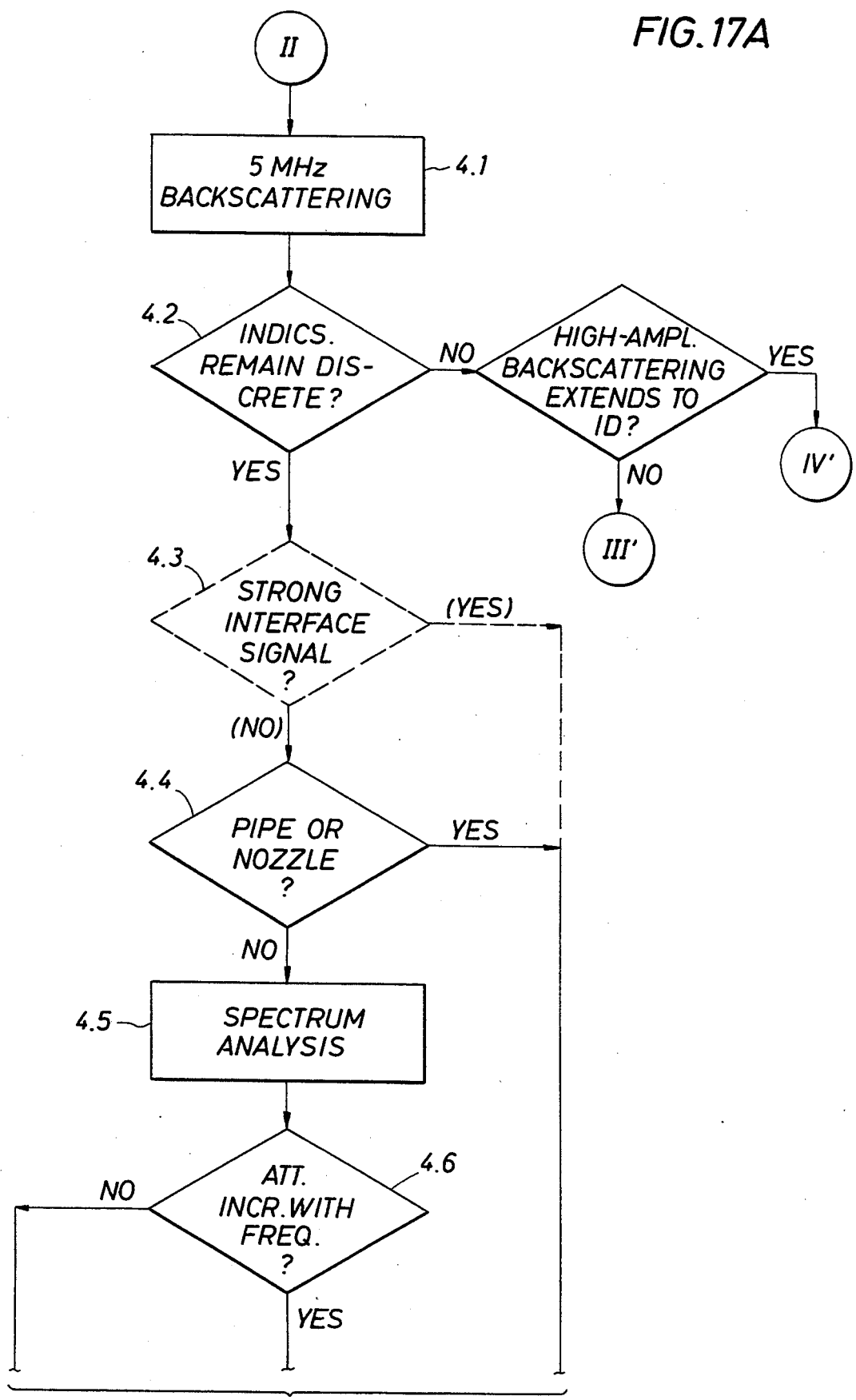
FIG. 17. Inspection procedure for locations showing Pattern II waveform.
Figure 17B:
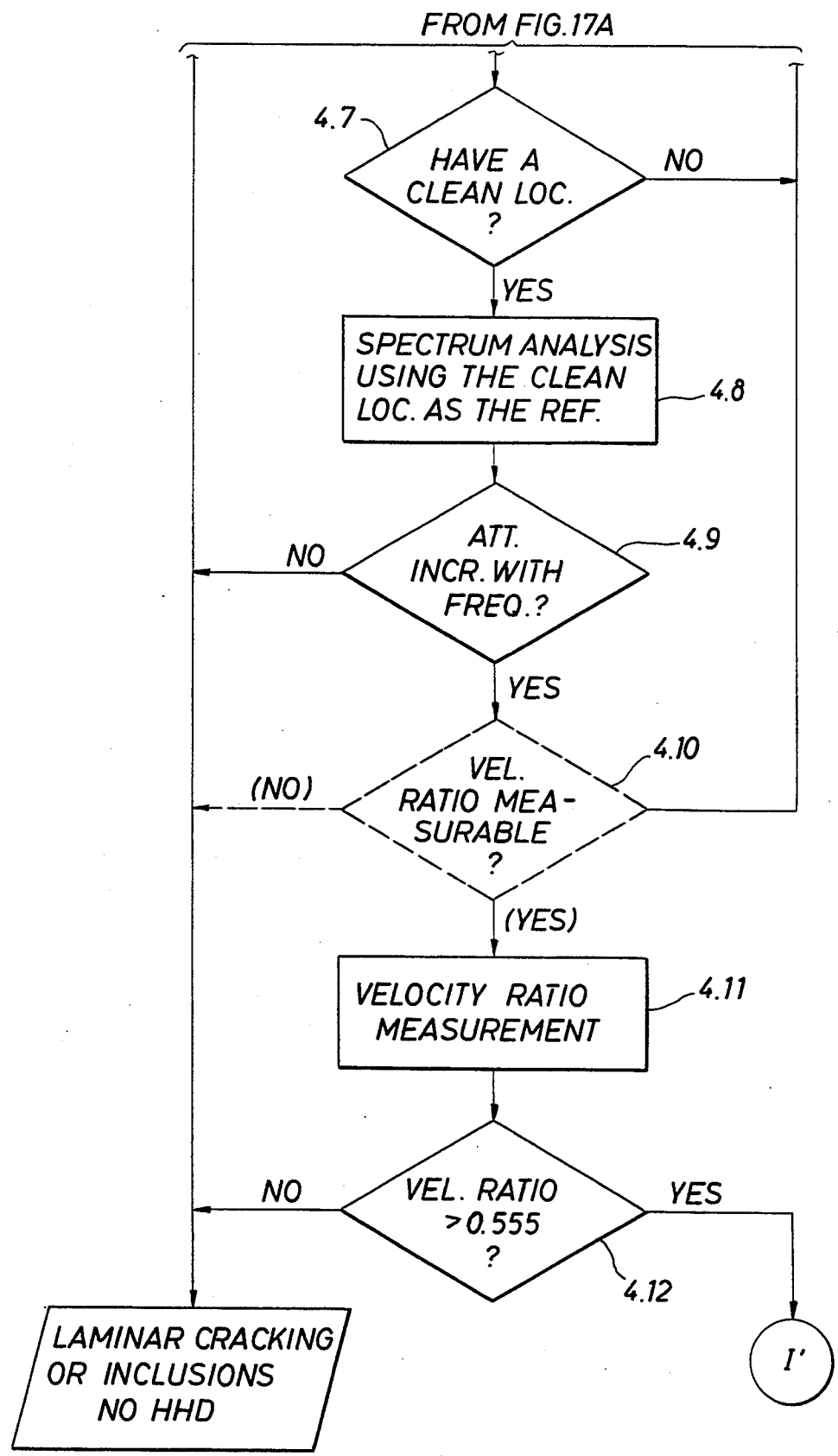

4. Pattern II: Discrete high-amplitude backscattering indications. The inspection procedure in this case is shown in FIG. 17 and described as follows. (Dashed lines indicate steps pertaining to inspection of clad equipment only.)

4.1 Conduct backscattering measurements using a 5 MHz/0.5" longitudinal wave transducer.

4.2 Go to step 6.1 if the discrete indications become a signal group and the group extends to the backwall echo or the interface signal (of clad equipment). Go to step 5.3 if the discrete indications become a signal group but the group does not extend to the backwall echo or the interface signal (of clad equipment). Continue to the next step if the indications remain discrete.

4.3 Skip steps 4.4–4.9 if the interface signal amplitude is greater than 5% of the backwall echo amplitude (for clad equipment only).

4.4 Skip steps 4.5–4.9 if the part under inspection is a piece of pipe or nozzle.

4.5 Conduct spectrum analyses using clean calibration block(s) as the reference.

4.6 If the resultant attenuation does not increase with frequency, measurements are completed for this spot.

4.7 Skip steps 4.8 and 4.9 if a clean location of the same geometry and thickness as the inspected location cannot be found.

4.8 Conduct spectrum analyses using the clean location as the reference.

4.9 If the resultant attenuation does not increase with frequency, measurements are completed for this spot.

4.10 If the interface signal (of clad equipment) is not clear enough for velocity ratio measurements, measurements are completed for this spot.

4.11 Conduct velocity ratio measurements.

4.12 Go to step 3.8 if the velocity ratio is greater than 0.555. Otherwise, measurements are completed for this spot.

Figure 18A:
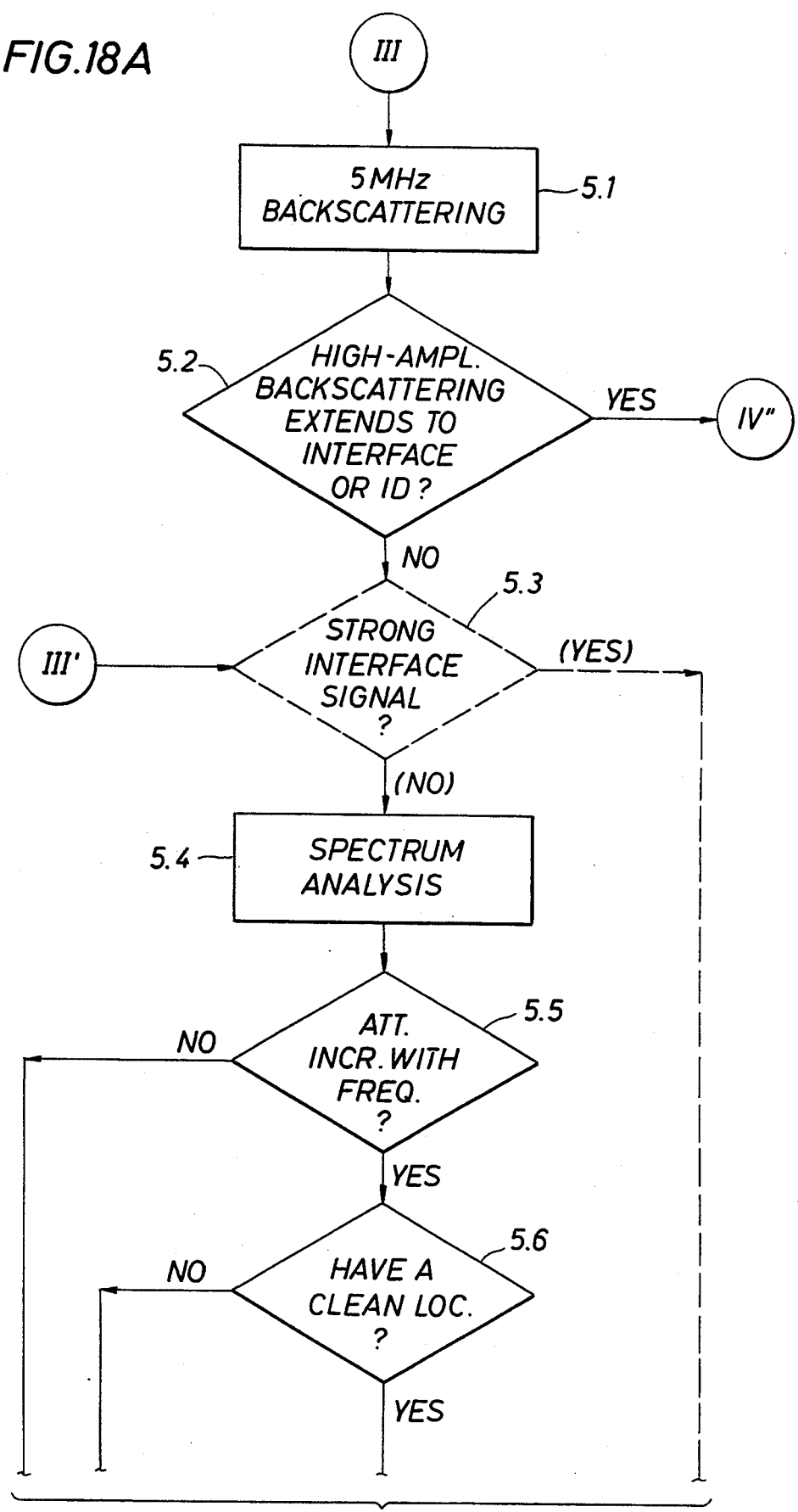
FIG. 18. Inspection procedure for locations showing Pattern III waveform.
Figure 18B:
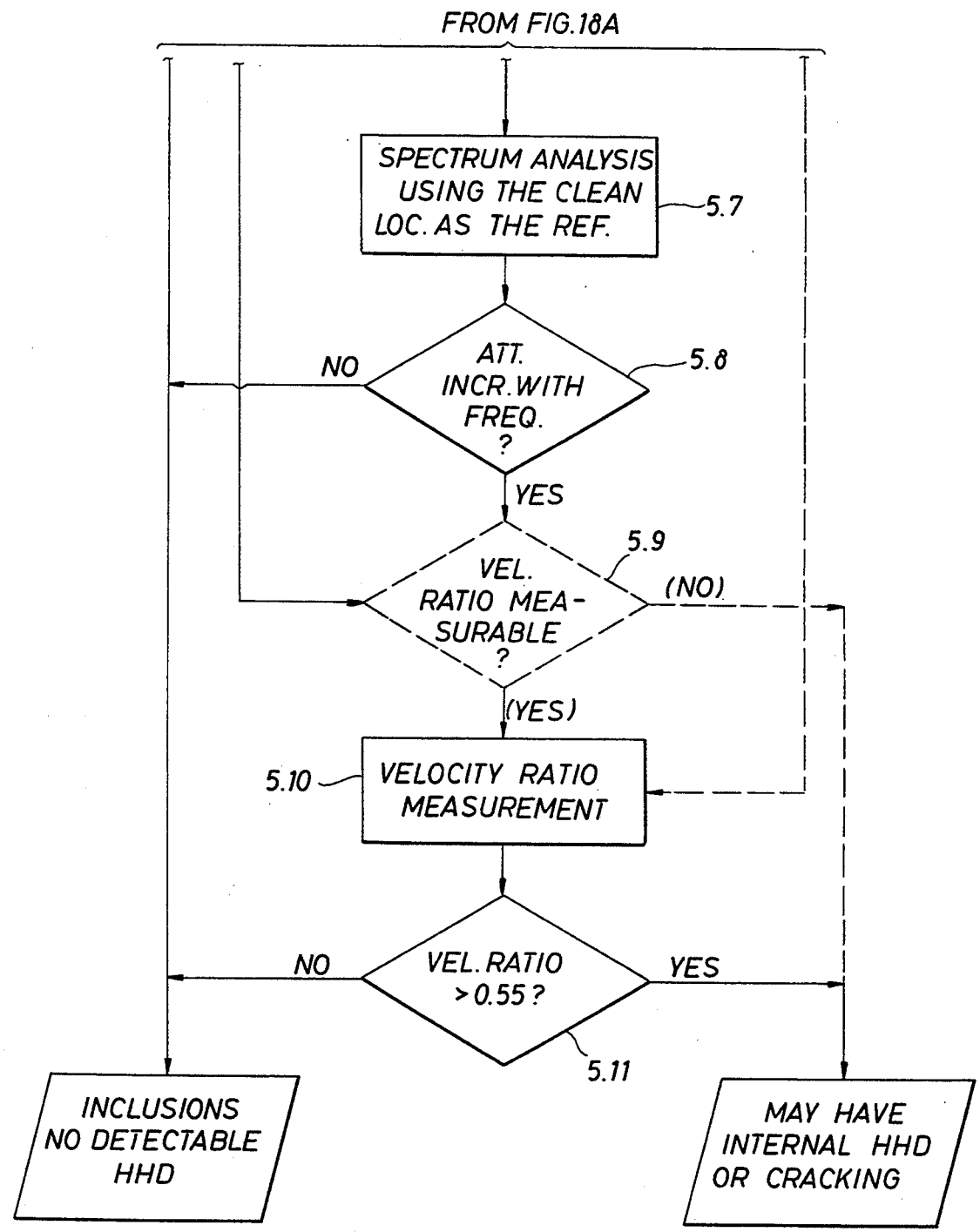

5. Pattern III: A group of high-amplitude backscattering signals at a distance from the backwall echo or the interface signal (of clad equipment). The inspection procedure in this case is shown in FIG. 18 and described as follows. (Dashed lines indicate steps pertaining to inspection of clad equipment only.)

5.1 Conduct backscattering measurements using a 5 MHz/0.5" longitudinal wave transducer.

5.2 Go to step 6.1 if the backscattering amplitude between the group of high-amplitude backscattering signals and the backwall echo or the interface signal (of clad equipment) increases as a result of the decrease of the transducer frequency.

NOTE: (For bare metals only) when the ID surface is accessible, conduct the following steps in place of steps 5.1 and 5.2: (1) Measure backscattering patterns from the ID surface by using a 10 MHz/0.5" longitudinal wave transducer. (2) Go to step 6.1 if the backscattering amplitude decreases continuously from the main bang signal to the backwall echo. Continue to step 5.3 if the result shows a group of high-amplitude backscattering signals at a distance from the ID, and the distance is the same as the distance between the group of high-amplitude backscattering signals and the backwall echo observed in the OD examination.

5.3 Skip steps 5.4–5.9 if the interface signal amplitude is greater than 5% of the backwall echo amplitude (for clad equipment only).

5.4 Conduct spectrum analyses using clean calibration block(s) as the reference.

5.5 If the resultant attenuation does not increase with frequency, measurements are completed for this spot.

5.6 Skip steps 5.7 and 5.8 if a clean location of the same geometry and thickness as the inspected location cannot be found.

5.7 Conduct spectrum analyses using the clean location as the reference.

5.8 If the resultant attenuation does not increase with frequency, measurements are completed for this spot.

5.9 Skip steps 5.10 and 5.11 if the interface signal is not clear enough for velocity ratio measurements (for clad equipment only).

5.10 Conduct velocity ratio measurements.

5.11 If the measured velocity ratio is not greater than 0.55, measurements are completed for this spot.

5.12 Measure the time of flight between the front of the high-amplitude backscattering signals and the 1st peak of the interface signal (of clad equipment) or the backwall echo (of bare materials). Record the time of flight as $\Delta t_{HA}$ in $\mu$sec.

5.13 Calculate and record the distance of possible damage progression as $d_{HA}=5.9 \cdot \Delta t_{HA}/2$ (mm).

5.14 Measurements are completed.

Figure 19A:
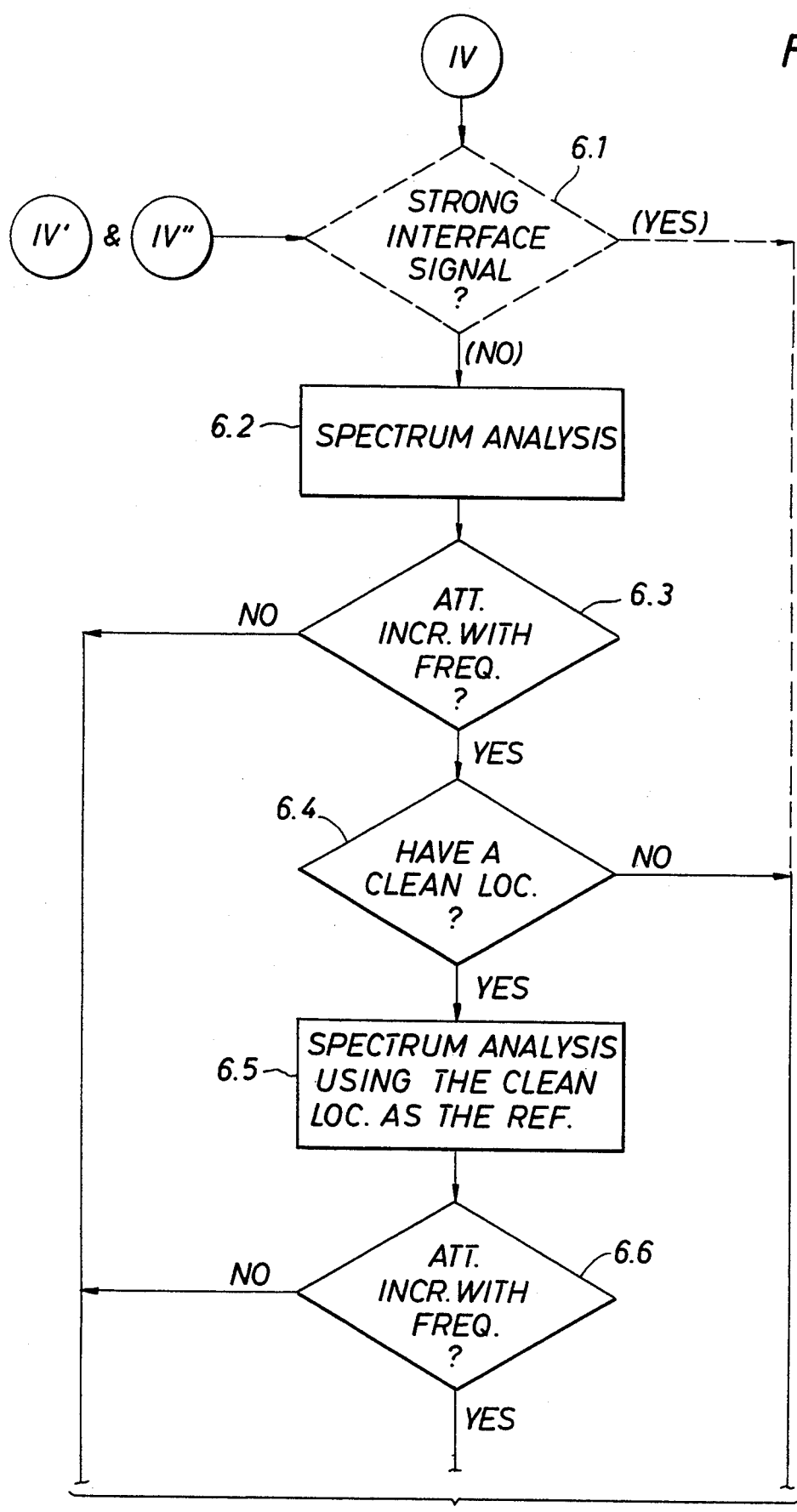
FIG. 19. Inspection procedure for locations showing Pattern IV waveforms.

6. Pattern IV: A group of high-amplitude backscattering signals extending from the backwall echo or the interface signal (of clad equipment). The inspection procedure in this case is shown in FIG. 19 and described as follows. (Dashed lines indicate steps pertaining to inspection of clad equipment only.)

6.1 Skip steps 6.2–6.6 if the interface signal amplitude is greater than 5% of the backwall echo amplitude (for clad equipment only).

6.2 Conduct spectrum analyses using clean calibration block(s) as the reference.

6.3 If the resultant attenuation does not increase with frequency, measurements are complete for this spot.

6.4 Skip steps 6.5 and 6.6 if a clean location of the same geometry and thickness as the suspect location cannot be obtained.

6.5 Conduct spectrum analyses using the clean location as the reference.

6.6 If the resultant attenuation does not increase with frequency, measurements are complete for this spot.

6.7 Skip steps 6.8 and 6.9 if the distance between the front of the high-amplitude backscattering signals and the 1st peak of the interface signal (of clad equipment) or the backwall echo (of bare materials) is not greater than 10% of the base metal thickness.

6.8 Skip step 6.9 if the interface signal is not clear enough for velocity ratio measurements (for clad equipment only).

6.9 Conduct velocity ratio measurements.

6.10 Measure the time of flight between the front of the high-amplitude backscattering signals and the first peak of the interface signal (of clad equipment) or the backwall echo (of bare materials). Record the time of flight as $\Delta t_{HA}$ in $\mu$sec.

6.11 Calculate and record the distance of possible damage progression as $d_{HA}=5.9 \cdot \Delta t_{HA}/2$ (mm).

6.12 Measurements are completed for this spot.

Table I may be used in conjunction with the flow charts, FIGS. 15–19, as an additional aid in determining the type of damage sustained by the equipment under test.

TABLE 1

| Condition | Backscattering | Spectrum Analysis | Velocity Ratio |
|---|---|---|---|
| HHD: initial stage | an increase of backscattering amplitude in front of ID | $\alpha$ increases with freq. higher-than nominal $\alpha$ at high freqs. | nominal |
| HHD: growing stage | strong internal backscattering decays toward ID; when measured from ID, backscatter ampl. decreases continuously toward OD. | high $\alpha$ and $\alpha$ increases with freq. | high velocity ratio |
| HHD: final stage | backscattering amplitude starts with $\alpha$ high value and then decreases continuously toward ID | high $\alpha$ and $\alpha$ increases with freq. | high velocity ratio |
| inclusion (in general) | moderate backscatter ampl. | slightly higher than nominal; $\alpha$ increases with freq. | nominal or may vary slightly from nominal |
| midwall inclusion | midwall backscatter (also true for measurement from internal surface) | slightly higher than nominal; $\alpha$ increases with freq. | nominal or may vary slightly from nominal |
| large grain size | moderate backscatter ampl. decreasing continuously toward ID | higher than nominal; $\alpha$ increases with freq. | nominal |
| scale on ID | nominal | high $\alpha$ at particular frequencies | nominal |
| non-parallel surfaces | nominal | high $\alpha$; $\alpha$ increases with freq. | nominal |
| rough ID surfaces | nominal | moderate or high $\alpha$ at high freqs. | nominal |
| pitting on the ID surface | a slight increase of backgcattering amplitude in front of ID | $\alpha$ increases with freq. higher-than-nominal $\alpha$ at high freq. | nominal |
| curved ID surface | nominal | $\alpha$ increases with freq. | nominal |
| disbond at clad/base metal interface | nominal in base metal; strong reflection from clad interface | high $\alpha$; $\alpha$ increase with freq. for partial disbonds | nominal in base metal |
| crack in cladding | nominal in base metal | higher than nominal | nominal in base |
| anisotropic weld overlay | nominal in base metal | higher than nominal | nominal in base metal |

What is claimed is:

1. A method for determining the presence of damage due to hydrogen attack in a material and mechanical properties of such damage:

a. performing amplitude-based backscattering tests to identify areas of the material which may be damaged;
b. performing a pattern-based backscattering test at each identified area, each pattern-based backscattering test providing a pattern which is classified as falling within at least one of four backscattering pattern category types, type I, type II, type III and type IV;
c. identifying the backscattering pattern type to determine what type of internal defect may exist in the material at that location,
   wherein the type I backscattering pattern is characterized by a continuous decrease of backscattering amplitude from a main bang signal to a backwall echo or an interface signal of clad equipment, the type I pattern indicating that the internal defect may be through-wall or nearly through-wall hydrogen attack,
   wherein the type II backscattering pattern is characterized by discrete high-amplitude backscattering indications, the type II pattern indicating that the internal defect may be a laminar defect instead of hydrogen damage,
   wherein the type III backscattering pattern is characterized by a group of high-amplitude backscattering signals at a distance from the backwall echo or the interface signal of clad equipment, the type III pattern indicating that the internal defect may be a growing stage of hydrogen attack,
   wherein the type IV backscattering pattern is characterized by a group of high-amplitude backscattering signals extending from the backwall echo or the interface signal of clad equipment, the type IV pattern indicating that the internal defect may be an initial or growing stage hydrogen attack;
d. sequentially performing appropriate follow-up tests and analyzing the results of each follow-up test for a positive indication of hydrogen attack before proceeding with the next follow-up test for each type of backscattering pattern identified for each location,
   wherein the follow-up tests for the type I pattern in sequential order are velocity ratio, spectrum analysis and spatial averaging backscattering, and the positive indication of hydrogen attack for each test is the velocity ratio is greater than 0.55, the spectrum analysis' attenuation increases with frequency and the spatial averaging backscattering's intensity distribution deviates significantly from clean references to hydrogen attack references,
   wherein the follow-up test for the type II pattern is a frequency-dependent backscatter test, the spectrum analysis, the velocity ratio, and the spectral averaging backscattering, and the positive indication of hydrogen attack for each test is the frequency-dependent backscattering's indications remain discrete, attenuation increases with frequency in the spectrum analysis, the velocity ratio is greater than 0.555, and the spatial averaging backscattering intensity distribution deviates significantly from clean references to hydrogen attach references,
   wherein the follow-up tests for the type III pattern are the frequency-dependent backscattering, the spectrum analysis, and the velocity ratio, and the positive indication of hydrogen attack for each test is the frequency-dependent backscattering's indications do not extend to material's clad interface or inside diameter, attenuation increases with frequency in the spectrum analysis, and the velocity ratio is greater than 0.55,
   wherein the follow-up test for the type IV pattern is the spectrum analysis and the velocity ratio, and the positive indication of hydrogen attack for each test is attenuation increases with frequency in the spectrum analysis, and the velocity ratio is greater than 0.55;
e. identifying the type of internal defect in the material from the follow-up tests performed in step (d),
   wherein the positive indications of hydrogen damage for the follow-up tests performed on the location having the type I pattern indicates that the internal defect is the through-wall or nearly through-wall hydrogen damage,
   wherein the positive indications of hydrogen damage for the follow-up tests performed on the location having the type II pattern indicates that the internal defect is the through-wall or nearly through-wall hydrogen damage instead of the defect being a laminar defect,
   wherein the positive indications of hydrogen damage for the follow-up tests performed on the location having the type III pattern indicates that the internal defect is at least one of the following two types of internal defects, the growing stage hydrogen damage and an internal cracking,
   wherein the positive indications of hydrogen damage for the follow-up tests performed on the location having the type IV pattern indicates that the internal defect is the growing stage or initial stage hydrogen attack;
f. determining the distance of the hydrogen attack damage progression from the pattern-based backscattering pattern; and
g. determining the mechanical properties of the hydrogen attack damage in the material, the mechanical properties being obtained are tensile elongation and mean value of the coefficient of hydrogen-attack-induced attenuation within the damaged thickness,
   wherein the tensile elongation is obtained by comparing the velocity ratio for the location under test with a chart featuring the tensile elongation as a function of velocity ratio for the same type of material, and
   wherein the coefficient of hydrogen-attack-induced attenuation within the damaged thickness is obtained by
   performing the spectrum analysis test at a reference location or on a calibration block having the same metallurgical and structural conditions to obtain a reference spectrum, the reference location or the calibration block being free of any hydrogen damage,
   subtracting the spectrum analysis obtained in step (d) from the reference spectrum, and
   calculating the coefficient of hydrogen-attack-induced attenuation.

* * * * *